(12) United States Patent
Yamaya et al.

(10) Patent No.: US 8,581,196 B2
(45) Date of Patent: Nov. 12, 2013

(54) DETECTOR-SHIFT TYPE COMBINED RADIATION THERAPY/PET APPARATUS

(75) Inventors: Taiga Yamaya, Chiba (JP); Hideo Murayama, Chiba (JP); Shinichi Minohara, Chiba (JP); Taku Inaniwa, Chiba (JP); Takuji Furukawa, Chiba (JP); Shinichirou Mori, Chiba (JP)

(73) Assignee: National Institute of Radiological Sciences, Chiba-shi (JP)

( * ) Notice: Subject to any disclaimer, the term of this patent is extended or adjusted under 35 U.S.C. 154(b) by 347 days.

(21) Appl. No.: 12/996,443

(22) PCT Filed: Aug. 1, 2008

(86) PCT No.: PCT/JP2008/063861
§ 371 (c)(1),
(2), (4) Date: Dec. 6, 2010

(87) PCT Pub. No.: WO2010/013345
PCT Pub. Date: Feb. 4, 2010

(65) Prior Publication Data
US 2011/0084211 A1 Apr. 14, 2011

(51) Int. Cl.
*G01T 1/161* (2006.01)
(52) U.S. Cl.
USPC .................................................. 250/363.03
(58) Field of Classification Search
USPC .................................................. 250/363.03
See application file for complete search history.

(56) References Cited

U.S. PATENT DOCUMENTS 5,949,080 A * 9/1999 Ueda et al. ............... 250/492.3
2005/0109943 A1 * 5/2005 Vaquero et al. .......... 250/363.04
2007/0153969 A1 * 7/2007 Maschke ........................... 378/4
2011/0092814 A1 * 4/2011 Yamaya et al. ............... 600/427

FOREIGN PATENT DOCUMENTS

| JP | U-2-48888 | 4/1990 |
| JP | A-4-268484 | 9/1992 |
| JP | A-9-211130 | 8/1997 |
| JP | A-2001-141827 | 5/2001 |
| JP | A-2001-346773 | 12/2001 |
| JP | A-2004-166975 | 6/2004 |
| JP | A-2005-52308 | 3/2005 |
| JP | A-2006-513410 | 4/2006 |
| JP | A-2007-3264 | 1/2007 |
| JP | A-2007-111535 | 5/2007 |
| JP | A-2007-206090 | 8/2007 |
| JP | A-2008-134205 | 6/2008 |
| JP | A-2008-173297 | 7/2008 |

OTHER PUBLICATIONS

Enghardt et al., "Charged hadron tumour therapy monitoring by means of PET," *Nuclear Instruments and Methods in Physics Research* Section A, 2004, pp. 284-288, vol. 525, Elsevier B.V.

(Continued)

*Primary Examiner* — Constantine Hannaher
(74) *Attorney, Agent, or Firm* — Oliff & Berridge, PLC

(57) ABSTRACT

In beam monitoring for detecting annihilation radiations produced by radiation irradiation in radiation therapy for cancer which is performed by irradiating the affected area by X-rays, gamma rays, or particle beams, a detector-shift type combined radiation therapy/PET apparatus is provided with an open PET device that includes a plurality of shiftable multi-ring detector rings; and a radiation irradiation device that is capable of irradiation with a radiation beam through between the detector rings. The apparatus changes the positions of the detector rings, performs irradiation with the radiation beam through between the detector rings, and then performs radiation measurement.

10 Claims, 25 Drawing Sheets

(56) References Cited

OTHER PUBLICATIONS

Janek et al., "Development of dose delivery verification by PET imaging of photonuclear reactions following high energy photon therapy," *Physics in Medicine and Biology*, Oct. 19, 2006, pp. 5769-5783, vol. 51, IOP Publishing Ltd., the UK.

Crespo et al., "On the detector arrangement for in-beam PET for hadron therapy monitoring," *Physics in Medicine and Biology*, Apr. 11, 2006, pp. 2143-2163, vol. 51, IOP Publishing Ltd., the UK.

Yamaya et al.., "A proposal of an open PET geometry," *Physics in Medicine and Biology*, Jan. 14, 2008, pp. 757-773, vol. 53, Institute of Physics and Engineering in Medicine, the UK.

Kitamura et al., "3D Continuous Emission and Spiral Transmission Scanning for High-Throughput Whole-Body PET," 2004, pp. 1-5, IEEE.

International Search Report for International Patent Application No. PCT/JP2008/063861, mailed on Oct. 7, 2008 (w/ English translation).

* cited by examiner

Fig. 4
(A)
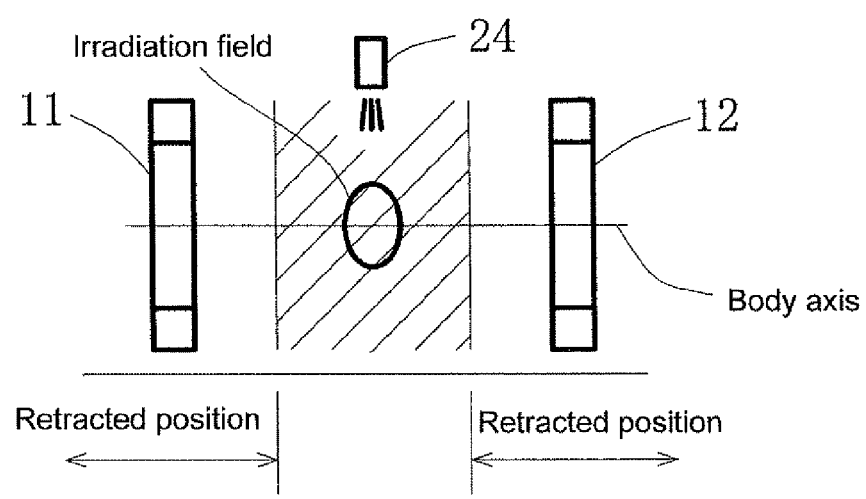
(B)
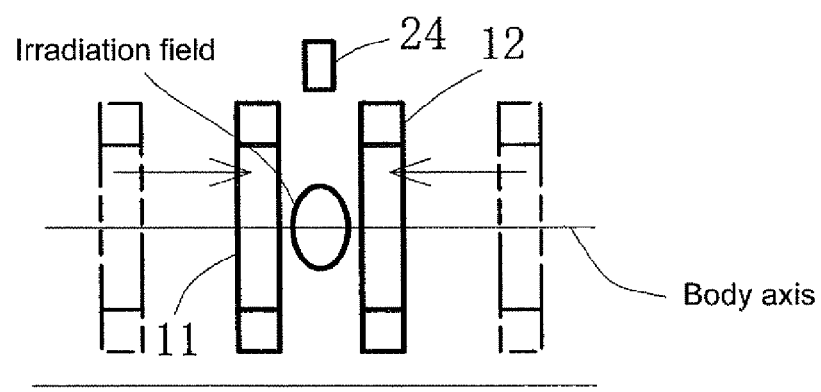

Fig. 5
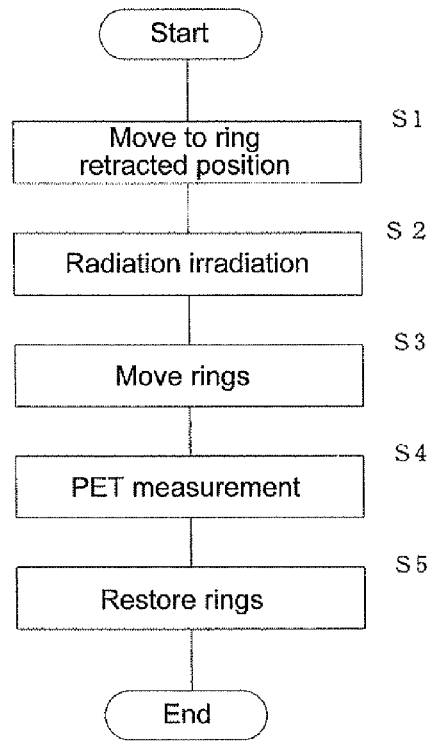
(A)
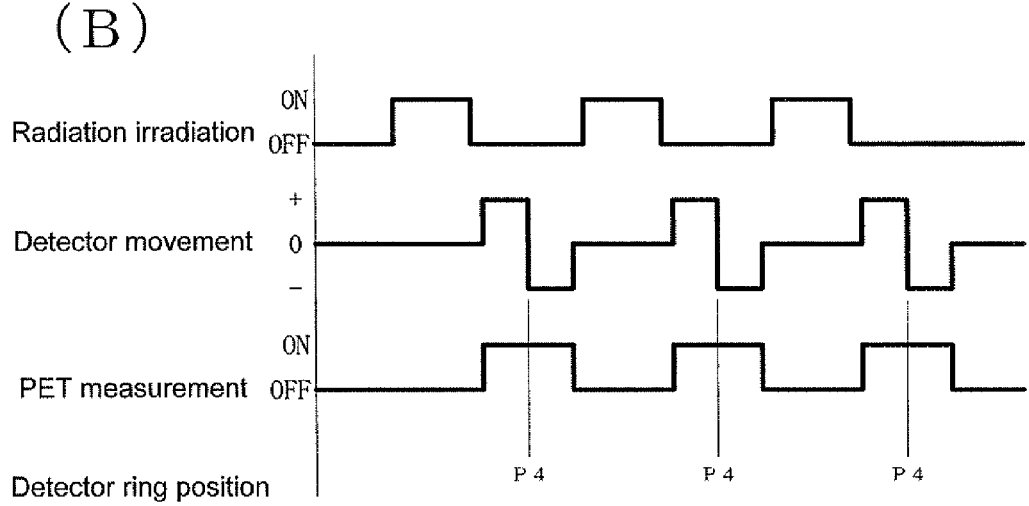
(B)

Fig. 7
(a) Six rings (outer rings fixed)
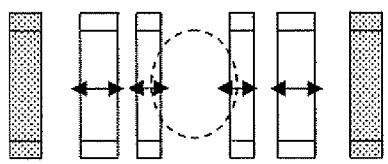
(b) Eight rings (two outer rings fixed)
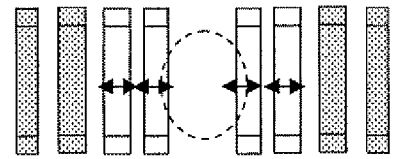
(c) Six rings (none fixed)
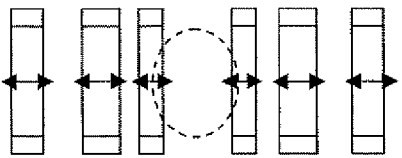
(d) Eight rings (three outer rings fixed)
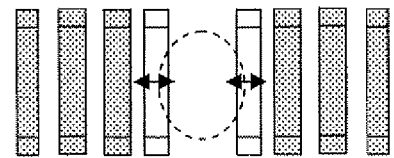
(Legend)  ◌ Open area    ▯ Moving detector    ▨ Fixed detector (b) Coordinates of the position of the detector center on the body axis (a) Sensitivity distribution

US 8,581,196 B2

DETECTOR-SHIFT TYPE COMBINED RADIATION THERAPY/PET APPARATUS

TECHNICAL FIELD

The present invention relates to a detector-shift type combined radiation therapy/PET device which can efficiently measure radiation occurring from short-lived nuclides at the time of monitoring for detecting annihilation radiation produced by radiation (also referred to as beam) irradiation in radiation therapy for cancer which is performed by irradiating the affected area with X-rays or particle beams, even if, in particular, the detectors are located away from the irradiation field during the beam irradiation.

BACKGROUND ART

Positron emission tomography (PET) is attracting attention as an effective test method for earlier diagnosis of cancer. In PET, a compound labeled with a trace amount of positron emitting nuclides is administered and annihilation radiation emitted from inside the body is detected to create an image of metabolic functions such as sugar metabolism and check for a disease and its extent. PET devices for practicing PET have been put into actual use.

The principle of PET will be described below. Positron emitted from a positron emitting nuclide by positron decay is annihilated with ambient electron to produce a pair of 511-keV annihilation radiations, which are measured by a pair of radiation detectors according to the principle of coincidence counting. The position of the nuclide can thus be located on a single line (coincidence line) that connects the pair of detectors. An axis from the patient's head to feet will be defined as a body axis. The distribution of nuclides on a plane that perpendicularly crosses the body axis is determined by two-dimensional image reconstruction from data on coincidence lines on the plane, measured in various directions.

Early PET devices therefore have had a single-ring detector in which detectors are closely arranged in a ring shape on a plane to be the field of view so as to surround the field of view. With the advent of a multi-ring detector which includes a lot of single-ring detectors closely arranged in the direction of the body axis, the two-dimensional field of view has subsequently been extended to three dimensions. Since 1990s, 3D mode PET devices have been actively developed which perform coincidence measurement even between detector rings with a significant improvement in sensitivity.

For cancer detected by the PET diagnosis or the like, treatments have a critical role. Approaches other than surgical operations and medication include radiation therapy of irradiating the affected area with radiations such as X-rays and gamma rays. In particular, particle radiotherapy of irradiating only a cancerous area with a heavy particle beam or proton beam is attracting much attention as a method both with an excellent treatment effect and a sharply concentrated irradiation characteristic with respect to the affected area. Among the methods of particle beam irradiation is conventional bolus irradiation where the irradiating beam is spread out to the shape of the affected area. In addition, spot scanning irradiation is under study, where the affected area is scanned with a pencil beam according to its shape and the like. In any case, the direction and dose of the irradiation beam are precisely controlled according to a treatment plan which is thoroughly calculated based on X-ray CT images or the like obtained separately.

The patient positioning accuracy is the key to administer treatment in precise accordance with the treatment plan. The irradiation field is often positioned based on an X-ray image. In general, X-ray images fail to provide a sufficient contrast between tumor and normal tissue, and it is difficult to identify a tumor itself for positioning. In addition to such misalignment of the irradiation field at the time of patient setup, other problems have been pointed out such as a change in the tumor size from the time of creation of the treatment plan, and respiratory and other movements of the tumor position. Under the present circumstances, it is difficult to accurately identify whether irradiation is performed according to the treatment plan. Even if the actual irradiation field deviates from the treatment plan, it is not easy to detect.

To solve the foregoing problems, attention is being given to a method of imaging the irradiation field in real time using the PET techniques. In the method, no PET medicine is administered. Instead, annihilation radiations produced by particle beam irradiation or X-ray irradiation through a projectile fragmentation reaction, target fragmentation reaction, and photonuclear reaction are rendered into an image by using the principle of PET. Therapy monitoring is possible since the position of occurrence of the annihilation radiations has a strong correlation with the dose distribution of the irradiation beam (W. Enghardt et al., "Charged hadron tumour therapy monitoring by means of PET," Nucl. Instrum. Methods A 525, pp. 284-288, 2004. S. Janek et al., "Development of dose delivery verification by PET imaging of photonuclear reactions following high energy photon therapy," Phys. Med. Biol., vol. 51 (2006) pp. 5769-5783).

In an ordinary PET device, detectors are arranged in a ring-like configuration. To install the detectors in combination with a treatment device, they need to be arranged so as not to interrupt the treatment beam. Studies have so far been made on an opposed gamma camera type PET device in which two flat PET detectors are installed across the bed of the treatment device. Such a PET device has had an essential problem that the detector gap causes a lack of information necessary for image reconstruction, resulting in nonuniform resolution and lower device sensitivity (P. Crespo et al., "On the detector arrangement for in-beam PET for hadron therapy monitoring," Phys. Med. Biol., vol. 51 (2006) pp. 2143-2163).

To improve the sensitivity of a PET device, as illustrated in FIG. 1(a), the detectors need to be closely arranged in a tunnel-like configuration to form a multi-ring detector 10 with a wide solid angle (in the diagram, the angle formed between two lines that connect the center of the maximum sensitivity area and the respective ends of the detector ring in the direction of the body axis). The long tunnel-shaped patient port, however, increases psychological stress on the patient 6 under examination as well as obstructs the patient's treatment. In view of this, the applicant has proposed an open PET device as exemplified in FIG. 1(b) in which a plurality of multi-ring detectors 11 and 12 split in the direction of the body axis of the patient 6 are arranged apart from each other to provide a physically opened area of field of view (also referred to as an open field of view). As shown in FIG. 2, images in the open area are reconstructed from the coincidence lines between the remaining multi-ring detectors 11 and 12. In the diagram, 8 represents a bed.

As shown in FIGS. 1(b) and 2, the open PET device is designed to have two split detectors of identical width (Taiga Yamaya, Taku Inaniwa, Shinichi Minohara, Eiji Yoshida, Naoko Inadama, Fumihiko Nishikido, Kengo Shibuya, Chih Fung Lam and Hideo Murayama, "A proposal of an open PET geometry," Phy. Med. Biol., 53, pp. 757-773, 2008). The open PET device is suitable for beam monitoring in radiation therapy since the beam irradiation can be performed without interfering with the detectors.

As shown in FIG. 3, the field of view is 2W+G in the direction of the body axis, where W is the dimension (also referred to as width) of the detectors 11 and 12 in the direction of the body axis, and G is the dimension (also referred to as gap) of the intervening open area between them in the direction of the body axis. As shown in FIG. 3(c), if the open area gap G exceeds W, the imaging area becomes discontinuous in the direction of the body axis. The upper limit of the open area gap G to obtain a field of view continuous in the direction of the body axis is thus W as shown in FIG. 3(b). However, the sensitivity concentrates at the center of the open area and drops significantly in the periphery of the open area. To suppress the extreme sensitivity drops at both ends of the open area, G needs to be set smaller than W as shown in FIG. 3(a). This, however, narrows the open area gap and the field of view in the direction of the body axis (see the foregoing document).

Since the open PET device previously proposed by the applicant has had the problem that the sensitivity concentrates at the center of the open area and drops significantly in the periphery of the open area, it has been needed to increase W relative to G in order to suppress the local sensitivity drops. The maximum values of the open area gap and the field of view in the direction of the body axis are limited to W and 3W, respectively. It has thus been needed to increase W itself in order to expand the open area gap and the field of view in the direction of the body axis further. In any case, there has been the problem that the increased number of detectors to constitute each multi-ring detector makes the device higher in price, larger in size, and more complicated in configuration.

For a conventional non-open PET device, a method of moving the PET device itself relative to the bed while performing radiation measurement has been used to measure a wider field of view with the detector ring of a limited field of view (Japanese Patent Application Laid-Open No. 2007-206090, Kitamura K, Takahashi S, Tanaka A et al., "3D continuous emission and spiral transmission scanning for high-throughput whole-body PET," Conf. Rec. IEEE NSS & MIC. M3-2, 2004). Such a method, however, provides no solution to the problems of the open PET device.

The open PET device is suitable for beam monitoring in radiation therapy since the beam irradiation can be performed via the gap between the detector rings without interfering with the detectors. The beam irradiation, however, may cause a performance drop or a failure of the detectors in cases such as when the detector circuit system is affected by the beam itself. During the beam irradiation, the detectors therefore need to be separated from the irradiation field by or more than a safe distance of several tens of centimeters. In order to expand the open area gap G, as mentioned previously, the dimension W of, the detectors in the direction of the body axis need to be increased. The upsizing of the device is undesirable, however, since it leads to higher price and limited installation location. There is another problem in that the solid angle decreases to lower the radiation detection sensitivity. It is known that the beam irradiation can produce a large amount of prompt gamma rays which serve as noise components to the PET measurement. The PET measurement data during the beam irradiation is often in a condition not suitable to imaging. Consequently, there is a need for a technology to stagger the irradiation and measurement time zones, thereby acquiring measurement data of high S/N ratio which is useful for image reconstruction. The radiation irradiation device and the PET device may be installed at a distance on the same rails so that the bed, after radiation irradiation, is moved from the radiation irradiation device to the PET device for measurement. Nevertheless, it takes time to transfer the bed while the nuclides produced by the radiation irradiation have an extremely short half-life of about several tens of seconds to 20 minutes. The nuclides may also move within the living body due to the blood flow and other factors. It is therefore not possible to approach the irradiation field in time. This being the case, it is needed to provide a technology for approaching the irradiation field by other methods and perform PET measurement as quickly as possible.

DISCLOSURE OF THE INVENTION

The present invention has been achieved to solve the foregoing conventional problems. It is thus an object of the present invention to prevent a performance degradation or a failure of the detectors due to the radiation irradiation, and create an image of the distribution of short-lived nuclides so as to cover up to the peripheral areas of the irradiation field.

The present invention includes: an open PET device including a plurality of detector rings that are arranged to be opposed to each other in a direction of a body axis and perform radiation measurement inside bores thereof; and a radiation irradiation device that is capable of irradiation with a radiation through a space between mutually-adjoining ones of the detector rings, thereby forming an irradiation field in the space. At least either one of two space-forming detector rings forming the space is a movable detector ring. The movable detector ring is located in a retreated position away from the irradiation field so as to avoid damage from irradiation during the radiation irradiation, and performs radiation measurement while moving on an irradiation-field side of the retreated position after the irradiation. Consequently, a performance degradation or a failure of the detectors due to the beam is prevented, and radiation measurement is performed in close proximity to the irradiation field to create an image of the distribution of short-lived nuclides in the vicinity of the irradiation field.

FIG. 4 shows the basic configuration of two detector rings and a radiation irradiation device. In FIG. 4, two movable detector rings 11 and 12 capable of moving in the direction of the body axis are opposed to each other. Radiation measurement is performed in the cylindrical hollow space area through the bores of the two detector rings. The radiation irradiation device 24 irradiates an irradiation field, which is established in the space area in the vicinity of the body axis, with radiation through the space that is formed between the two detector rings 11 and 12 (space-forming detector rings). FIG. 4(A) shows a state where both the detector rings 11 and 12 are in a retracted position (which refers to respective positions away from the irradiation field so as to avoid damage from the radiation irradiation; outside of the shaded area). FIG. 4(B) shows a state where both the detector rings 11 and 12 move from the retracted position shown in FIG. 4(A) toward the irradiation field, coming closest to the irradiation field after the end of the radiation irradiation.

The operating order of the two space-forming detector rings and the radiation irradiation device of FIG. 4 will be described with reference to the flowchart shown in FIG. 5(A). Each detector ring reciprocates between its retracted position and the proximity of the irradiation field. More specifically, the detector rings are moved to the retracted position (S1) before radiation irradiation. In such a position, it is not possible to create a precise image of the irradiation field due to a significant drop in sensitivity in the periphery of the open area, as well as a small solid angle. When the radiation irradiation (S2) ends, the detector rings are then immediately moved from the retracted position toward the irradiation field (S3), thereby compensating a drop in sensitivity in the periphery of the open area for radiation measurement (S4). The detector rings are restored to the retracted position (S5). Here, the measurement of PET at step S4, i.e., the radiation measurement for obtaining data useful for image reconstruction will be referred to as PET measurement. The same holds for the following.

The operating timing of each component in the foregoing operation will be described with reference to the time chart shown in FIG. 5(B). The time chart shows the ON and OFF of the radiation irradiation, the direction of movement of the detectors (+: on an approach toward the irradiation field, −: on a return away from the irradiation field, 0: at rest), the ON and OFF of the PET measurement, and the position of the detector rings. When the radiation irradiation ends, the detector rings in the retracted position immediately start moving on the approach toward the irradiation field. At the same time, it becomes possible to perform the PET measurement. Reaching a predetermined position (P4) closest to the irradiation field, the detection rings reverse their direction of movement and move on the return toward the retracted position. The detection rings reach the retracted position, and the PET measurement ends. When a next radiation irradiation is started, the foregoing pattern is repeated. The repetition lasts until the end of the irradiation plan.

Hereinafter, the configuration and moving pattern of the detector rings will be described in detail.

FIG. 6 shows typical patterns of the configuration and moving directions of the detector rings. FIG. 6(a) shows a configuration where two split detection rings 11 and 12 both are movable with an open area therebetween. FIG. 6(b) shows a configuration where two split detector rings (21, 22), (23, 24) are arranged on the right and on the left. The two outer detector rings 21 and 24 are fixed. The two center detector rings 22 and 23 are movable with an open area therebetween. FIG. 6(c) shows a configuration where three split detector rings (31, 32, 33), (34, 35, 36) are arranged on the right and on the left. The four outer detector rings 31, 32, 35, and 36 are fixed. The two center detector rings 33 and 34 are movable. The space between the movable center detector rings 33 and 34 is the open area.

In any case, the movable detector rings may be moved in directions such as shown in FIG. 6. The examples include where the two detector rings move toward each other (reducing the gap), the two shift with a certain distance therebetween (parallel), and the two move in the same direction with the gap increasing or decreasing. The movable detector rings may be moved in one way or two ways. Either one of the detector rings may be moved alone.

FIG. 7 shows configuration examples where the number of movable detector rings or the number of rings is increased.

The PET measurement may be performed either continuously in motion or at rest after moves. During the measurement, the moving speed may be changed. The move and rest may be repeated in small steps. The step width may be changed.

In the present invention, the detectors are located away from the irradiation field during beam irradiation. The detectors are moved toward the irradiation field immediately after the end of the beam irradiation as quickly as possible so that the PET measurement is performed with a large solid angle. The PET measurement is also performed on the approach, collecting more PET measurement data. This makes it possible to measure radiation occurring from short-lived nuclides efficiently with a high S/N ratio.

Since local sensitivity drops in the open area are suppressed, it is possible to improve the image quality of the entire open space including the peripheral areas as well as the center of the open space.

BRIEF DESCRIPTION OF THE DRAWINGS

FIG. 4 is a diagram showing the relationship between space-forming rings and an irradiation field;

FIG. 5 includes a flowchart and a time chart showing the operation of movable detector rings;

FIG. 7 is a diagram showing configuration examples other than those of FIG. 6;

BEST MODE FOR CARRYING OUT THE INVENTION

Hereinafter, embodiments of the present invention will be described in detail with reference to the drawings.

The configuration and the detection sensitivity distribution of the detector rings will be described.

Figure 1:
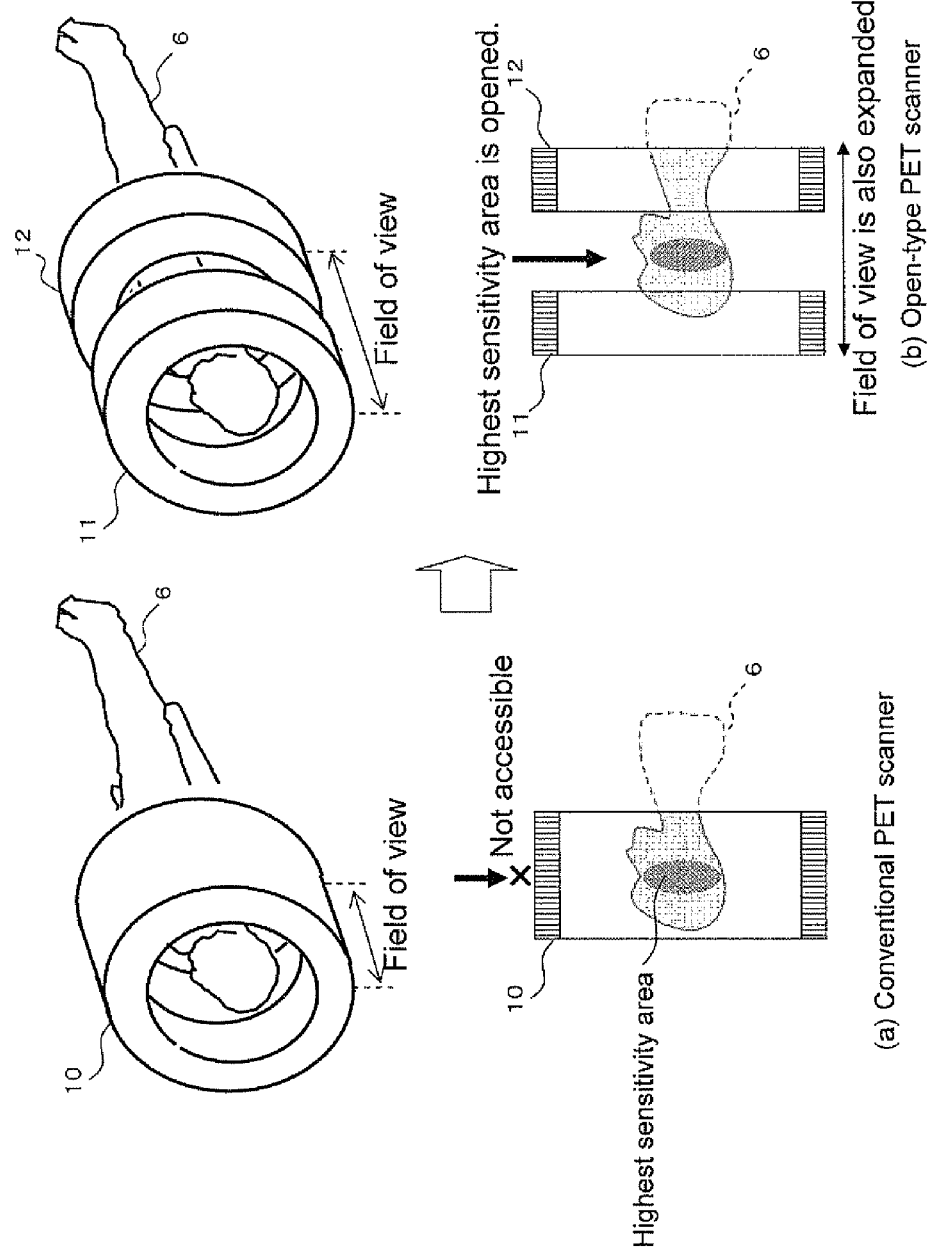
FIG. 1(a) includes a perspective view and a cross-sectional view showing the configuration of a conventional typical PET device, and FIG. 1(b) includes a perspective view and a cross-sectional view showing the configuration of an open PET device that has previously been proposed by the applicant.
Figure 2:
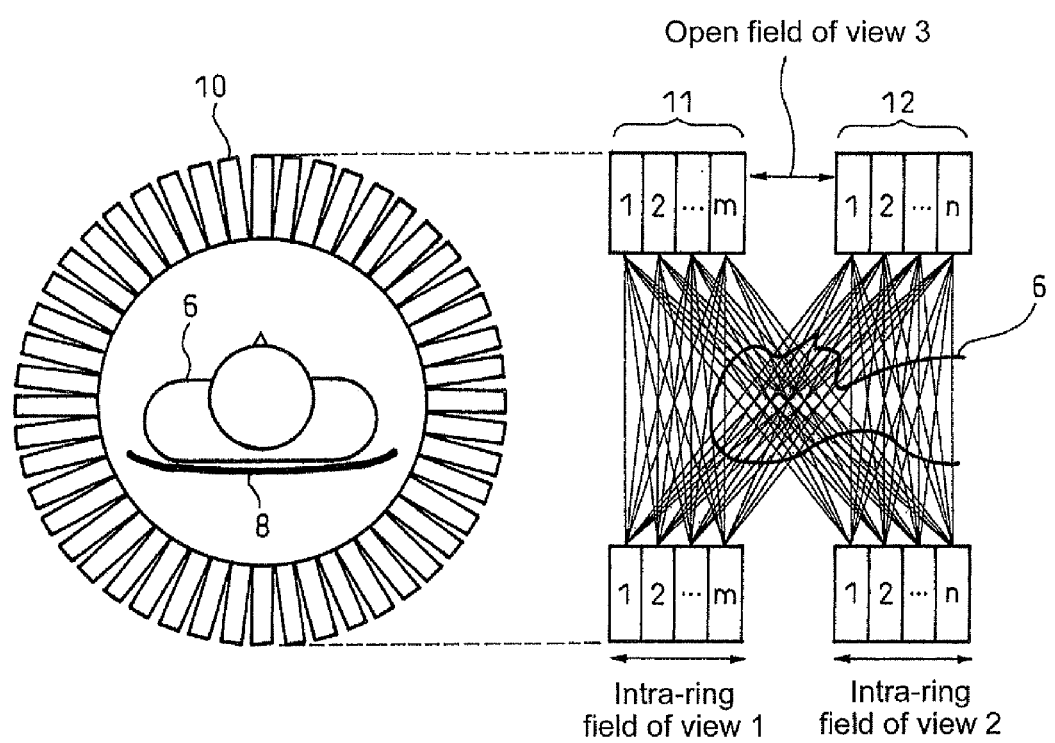
FIG. 2 is a cross-sectional view showing the principle of image reconstruction in an open PET device.
Figure 3:
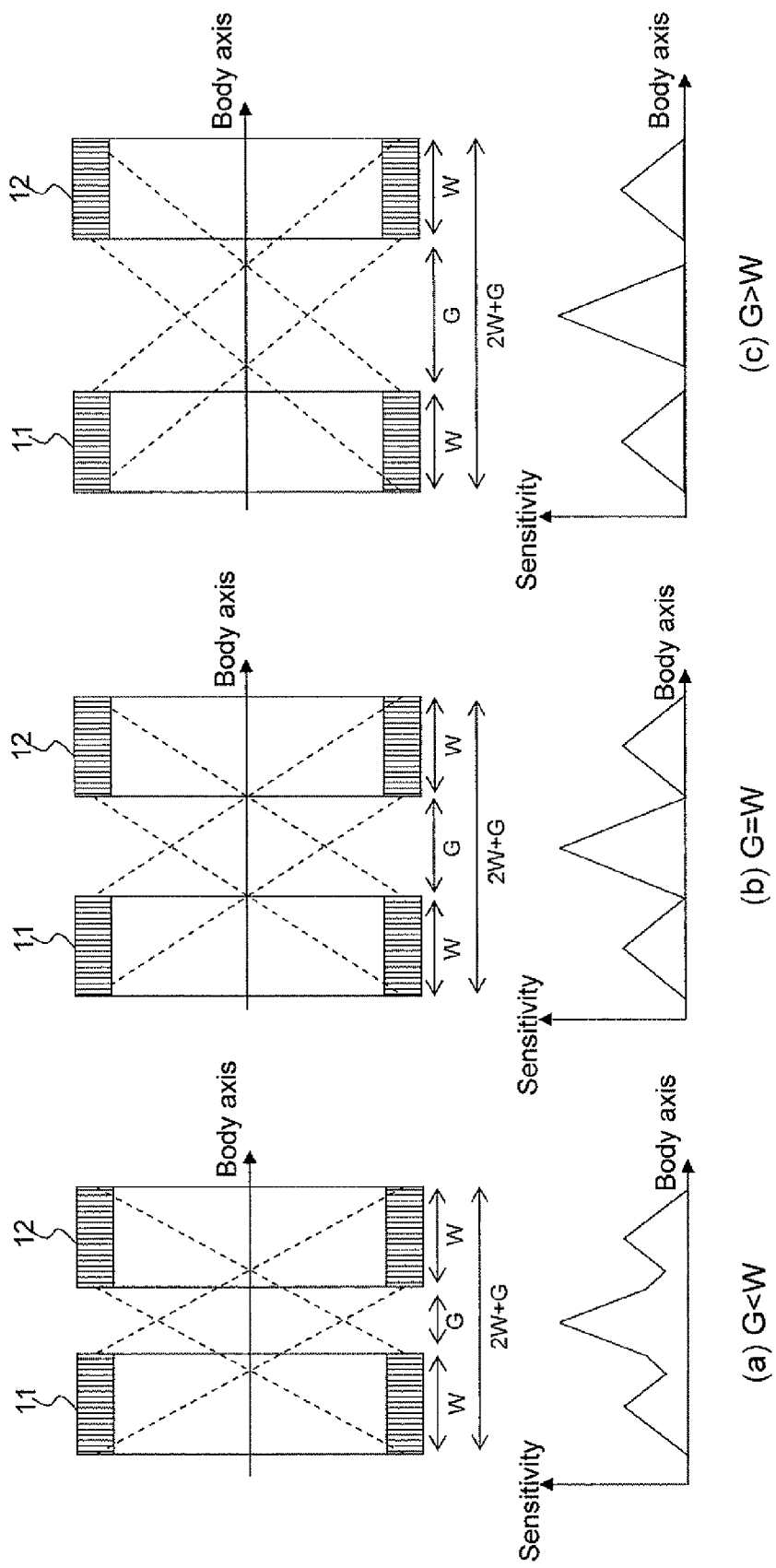
FIG. 3 includes cross-sectional views and graphs showing the relationship between the open area gap and sensitivity of an open PET device.
Figure 6:
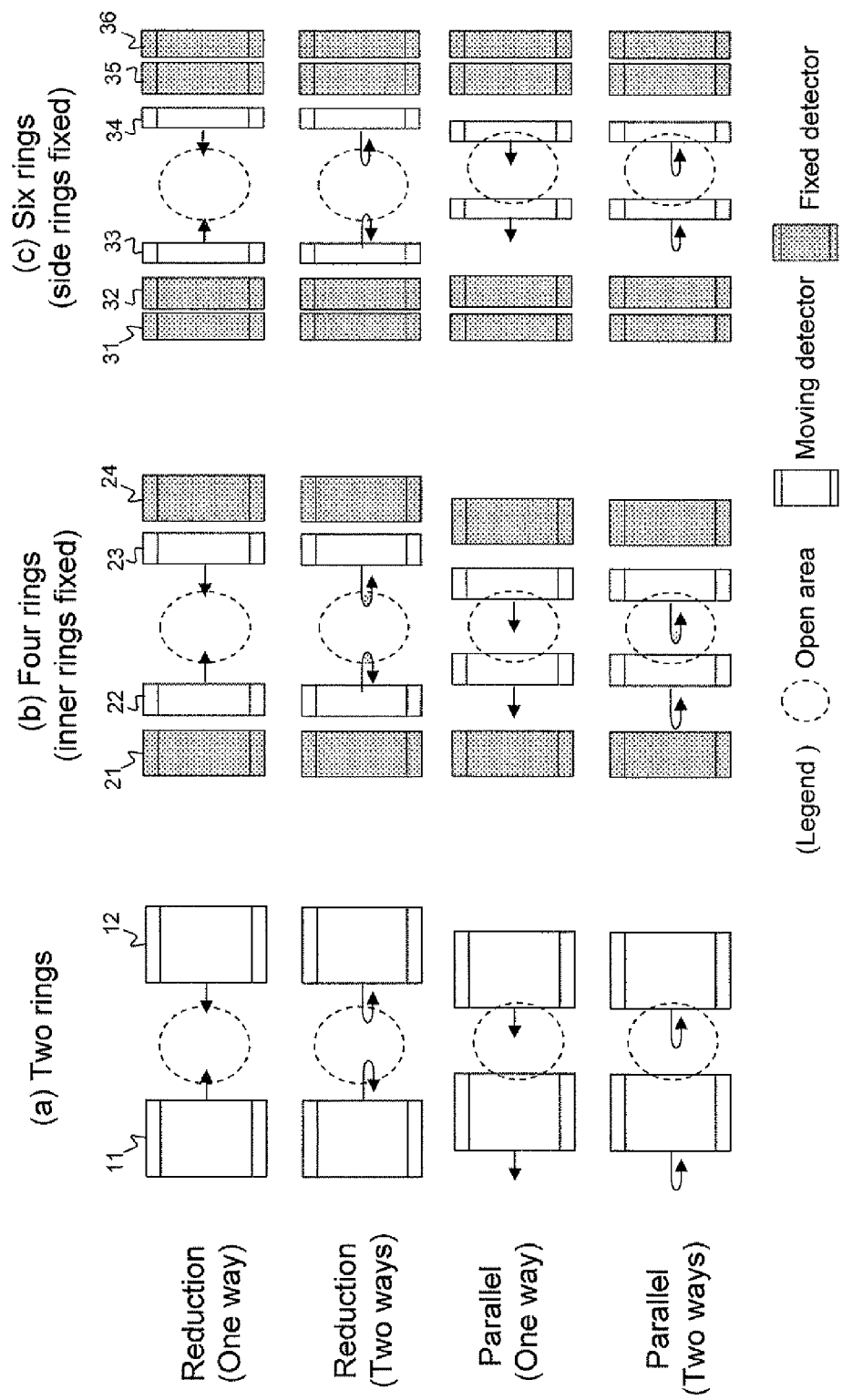
FIG. 6 is a diagram showing configuration examples of the open PET device for use in the present invention.
Figure 8:
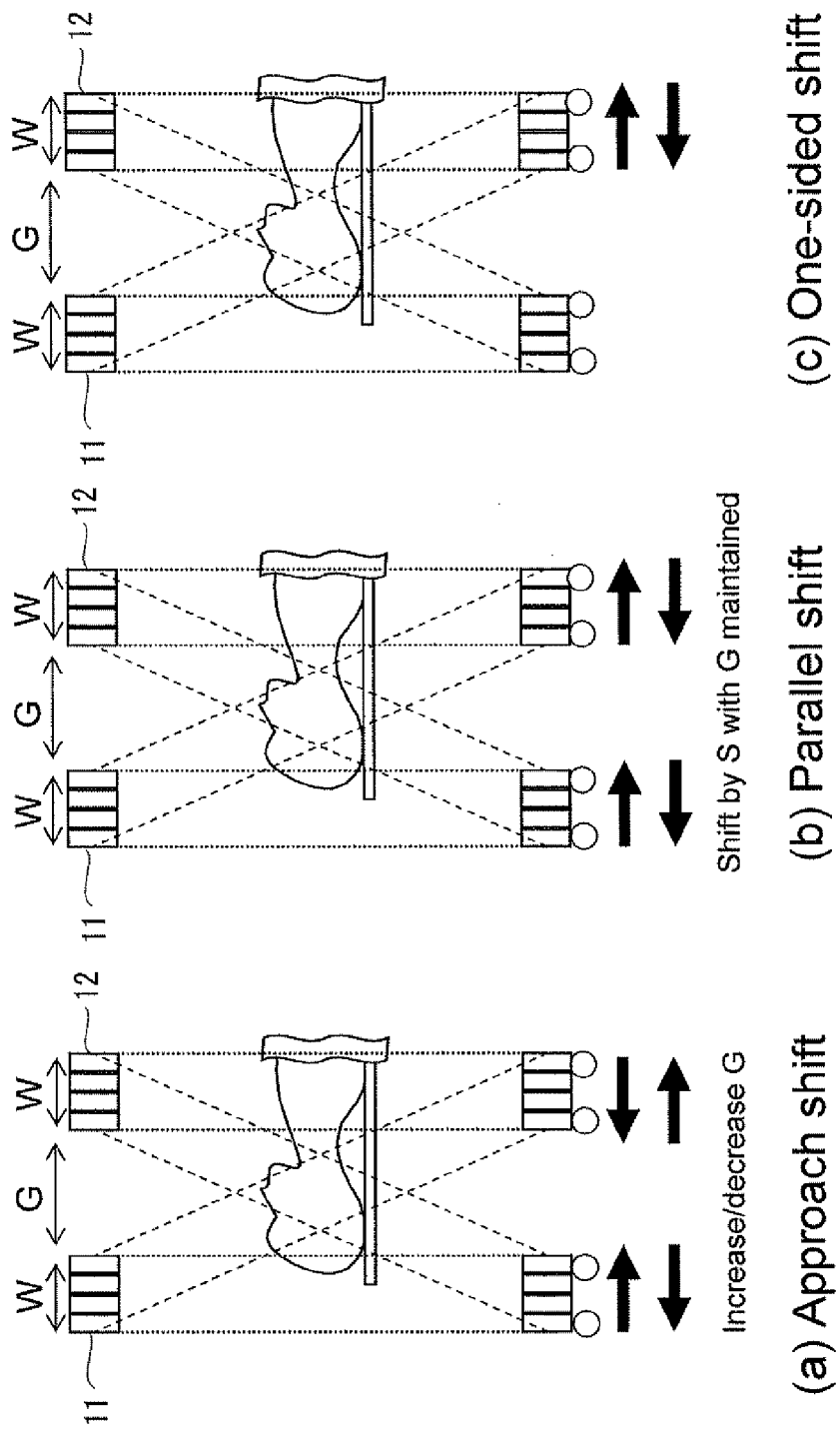
FIG. 8 is a diagram showing the states of (a) an approach shift, (b) a parallel shift, and (c) a one-sided shift according to a configuration example of the present invention.

Based on a commercially available PET device, a computer simulation was performed for situations where detector rings 11 and 12 were horizontally arranged apart as shown in FIG. 8, the detector rings being composed of 32 detection element rings (4.8 mm in width) each including 576 detector elements (scintillators) arranged on a circumference with a diameter of 827 mm. The detector ring width W was 153.6 mm.

The moving directions tested include where the open area gap G decreases and increases as shown in FIG. 8(*a*) (referred to as an approach shift), where the right and left detector rings shift by S with the open area gap G maintained constant as shown in FIG. 8(*b*) (referred to as a parallel shift), and where either one of the detector rings shifts by itself as shown in FIG. 8(*c*) (referred to as a one-sided shift).

Figure 9:
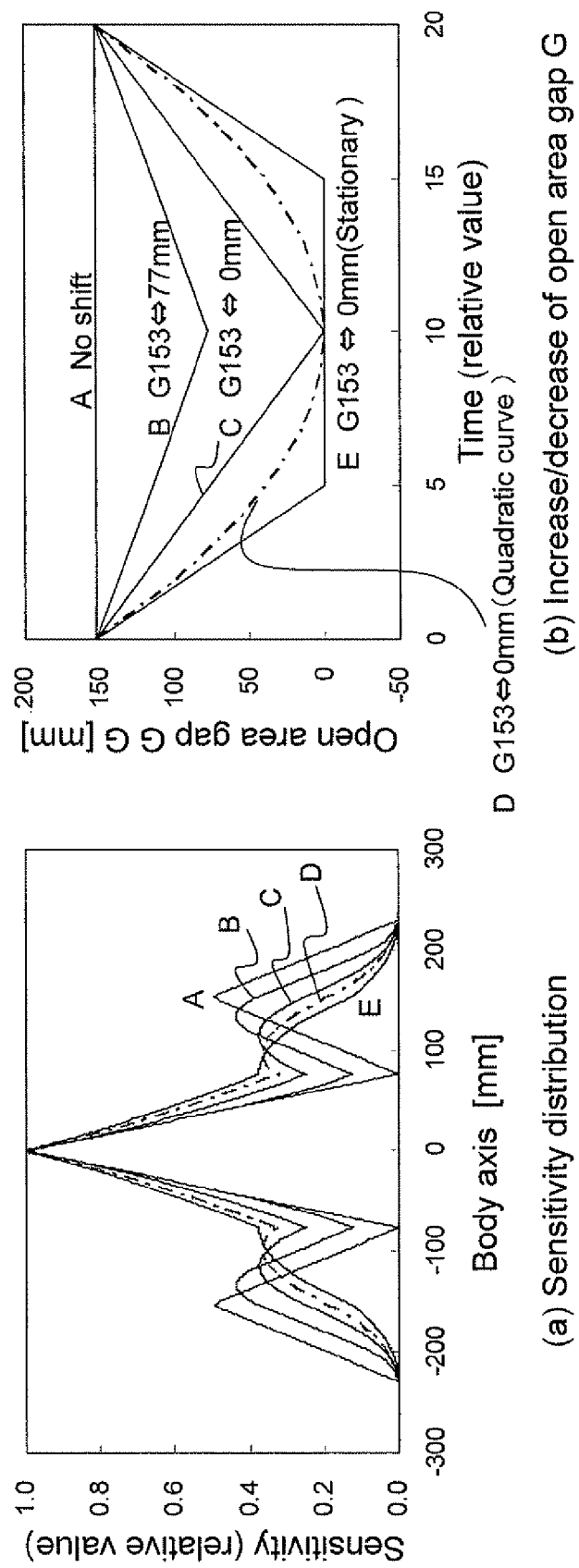
FIG. 9 is a diagram showing examples of (a) the sensitivity distribution and (b) the decreasing and increasing pattern of the open area gap with an approach shift.

FIG. 9 shows the results of trials with an approach shift. FIG. 9(*a*) shows sensitivity distributions resulting from five moving methods A to E. FIG. 9(*b*) shows time variations of the open area gap G. A shows a conventional case where the detector rings are fixed at G=153 mm. Significant drops are observed in the sensitivity distribution. B and C are where G is reduced from 153 mm to 77 mm and 0 mm at constant speed, respectively, and then increased to 153 mm again at constant speed. It can be seen that the sensitivity drops which were observed in the conventional case are suppressed. E is where the moving speed of C is doubled, with an additional rest at G=0 mm. It is shown that the longer stay of the detector rings at the device center improves the sensitivity characteristic further. D is an example where the moving speed of C is modified into a quadratic curve. As with E, the sensitivity characteristic is improved. The mechanical load to turn back the detector rings can also be reduced.

Figure 10:
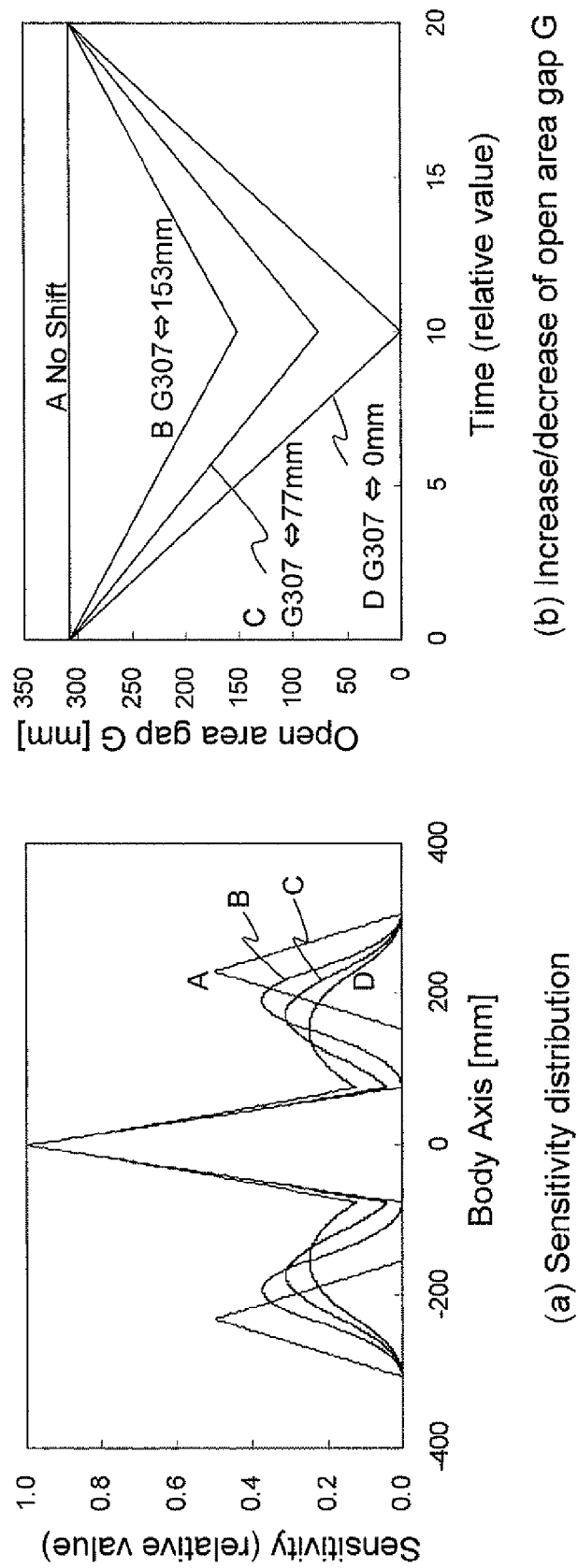
FIG. 10 is a diagram showing examples of (a) the sensitivity distribution and (b) the decreasing and increasing pattern of the open area gap with an approach shift, the examples being other than those of FIG. 9.

FIG. 10 shows the results of similar trials with an approach shift, whereas the open area gap G had an initial value of 307 mm. FIG. 10(*a*) shows sensitivity distributions resulting from four moving methods A to D. FIG. 10(*b*) shows time variations of the open area gap G. A shows a conventional case where the detector rings are fixed at G=307 mm. There are two dead regions of considerable size. B to D are where G is reduced from 307 mm to 153 mm, 77 mm, and 0 mm at constant speed, respectively, and then increased to 307 mm again at constant speed. It can be seen that the sensitivity drops which were observed in the conventional case are suppressed. In any case, the approach shift characteristically has the same peak value at the center of the sensitivity distribution.

Figure 11:
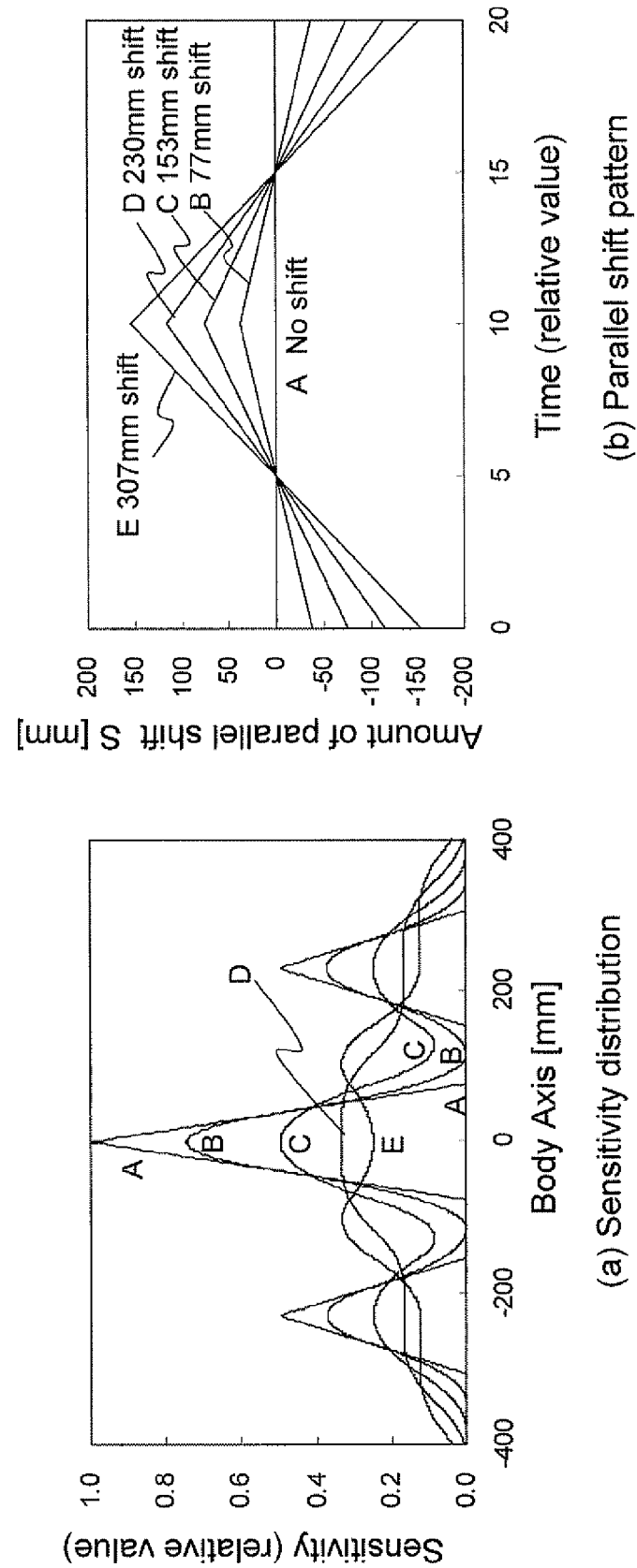
FIG. 11 is a diagram showing examples of (a) the sensitivity distribution in a parallel shift and (b) the parallel shift pattern.

FIG. 11 shows the results of trials with a parallel shift, where the open area gap is fixed at G=307 mm. FIG. 11(*a*) shows sensitivity distributions resulting from five moving methods A to E. FIG. 11(*b*) shows the parallel shift patterns. The detector rings were shifted to reciprocate at constant moving speed. A shows a conventional case where the detector rings are fixed. Significant drops and dead regions are observed in the sensitivity distribution. B to D are where the detector rings are shifted by 77 mm, 153 mm, and 230 mm, respectively. It can be seen that the peak of the sensitivity distribution scatters and the uniformity of the sensitivity distribution improves with the increasing amount of shift. E is the case where the detector rings are shifted up to 307 mm. A comparison with D shows that new sensitivity peaks appear conversely.

Figure 12:
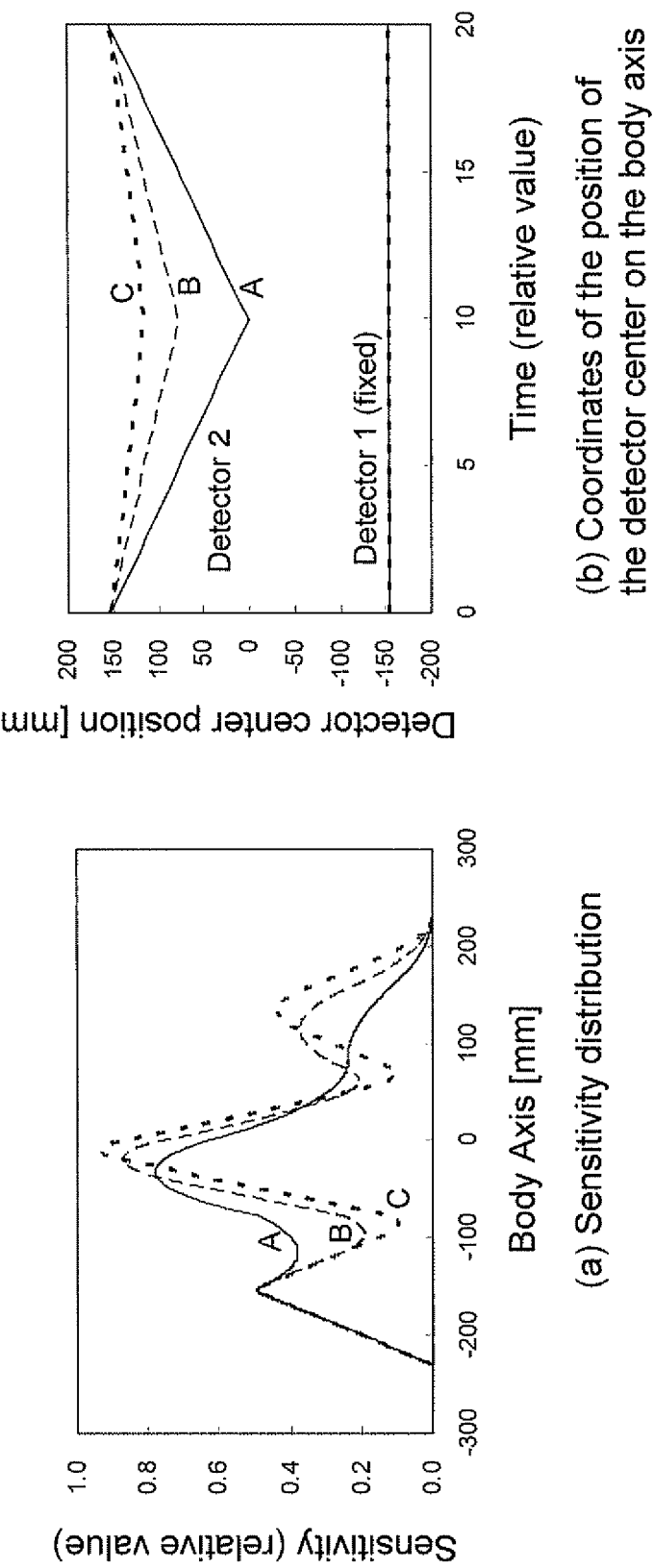
FIG. 12 is a diagram showing examples of (a) the sensitivity distribution and (b) the coordinates of the positions of the detector centers on the body axis with a one-sided shift.

FIG. 12 shows the results of trials with a one-sided shift. FIG. 12(*a*) shows sensitivity distributions resulting from three moving methods A to C. FIG. 12(*b*) shows the coordinates of the detector centers of the left and right detector rings (detector 1 and detector 2) on the body axis. In each case, the detector 1 is stationary and the detector 2 alone is movable. The gap at time 0 is G=153 mm. In A to C, the gap is reduced down to 0 mm, 77 mm, and 115 mm, respectively. The sensitivity peak of the shifted detector 2 (right in the chart) is dispersed to suppress the local sensitivity drops in the open area.

Figure 13:
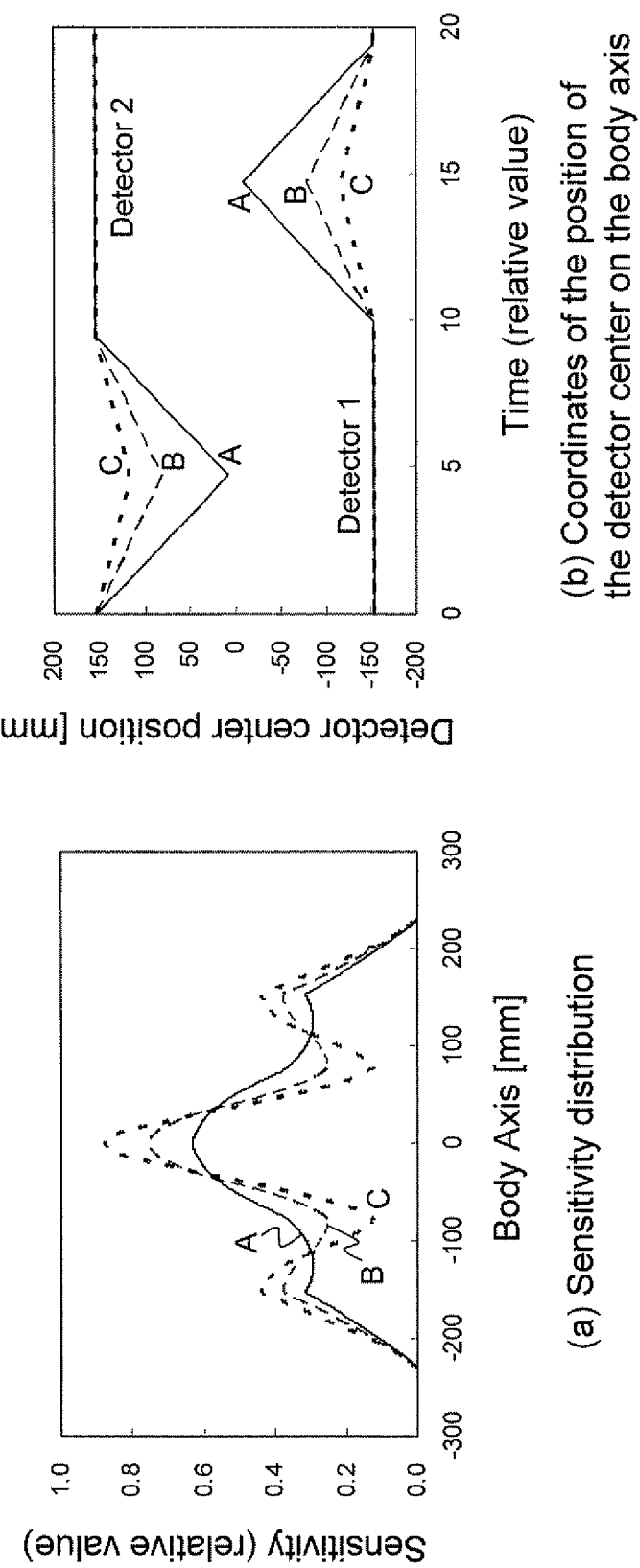
FIG. 13 is a diagram similarly showing other examples of (a) the sensitivity distribution and (b) the coordinates of the positions of the detector centers on the body axis with a one-sided shift.

FIG. 13 shows the results of trials with a one-sided shift where the stationary detector ring is switched. FIG. 13(*a*) shows sensitivity distributions resulting from three moving methods A to C. FIG. 13(*b*) shows the coordinates of the detector centers of the left and right detector rings (detector 1 and detector 2) on the body axis. In each case, the detector 1 is stationary and the detector 2 is movable between time 0 and 10. The detector 2 is stationary and the detector 1 is movable between time 10 and time 20. The gap at time 0 is G=153 mm. A to C are cases where the minimum gap is 0 mm, 77 mm, and 115 mm, respectively. It can be seen that the sensitivity peak is dispersed to suppress the local sensitivity drops. The effect is symmetrical, and increases with the increasing amount of shift.

An open PET device with two split detector rings has a sensitivity distribution that has a center peak and about half peaks on the right and left. The approach shift maintains the center peak and shifts the right and left peaks toward the center to fill the sensitivity recesses. Such a method improves the image quality of the open area alone. The parallel shift has the effect of flattening out the sensitivity peaks to fill the sensitivity recesses. Such a method improves the image quality of not only the open area but also the entire field of view along the body axis.

Figure 14:
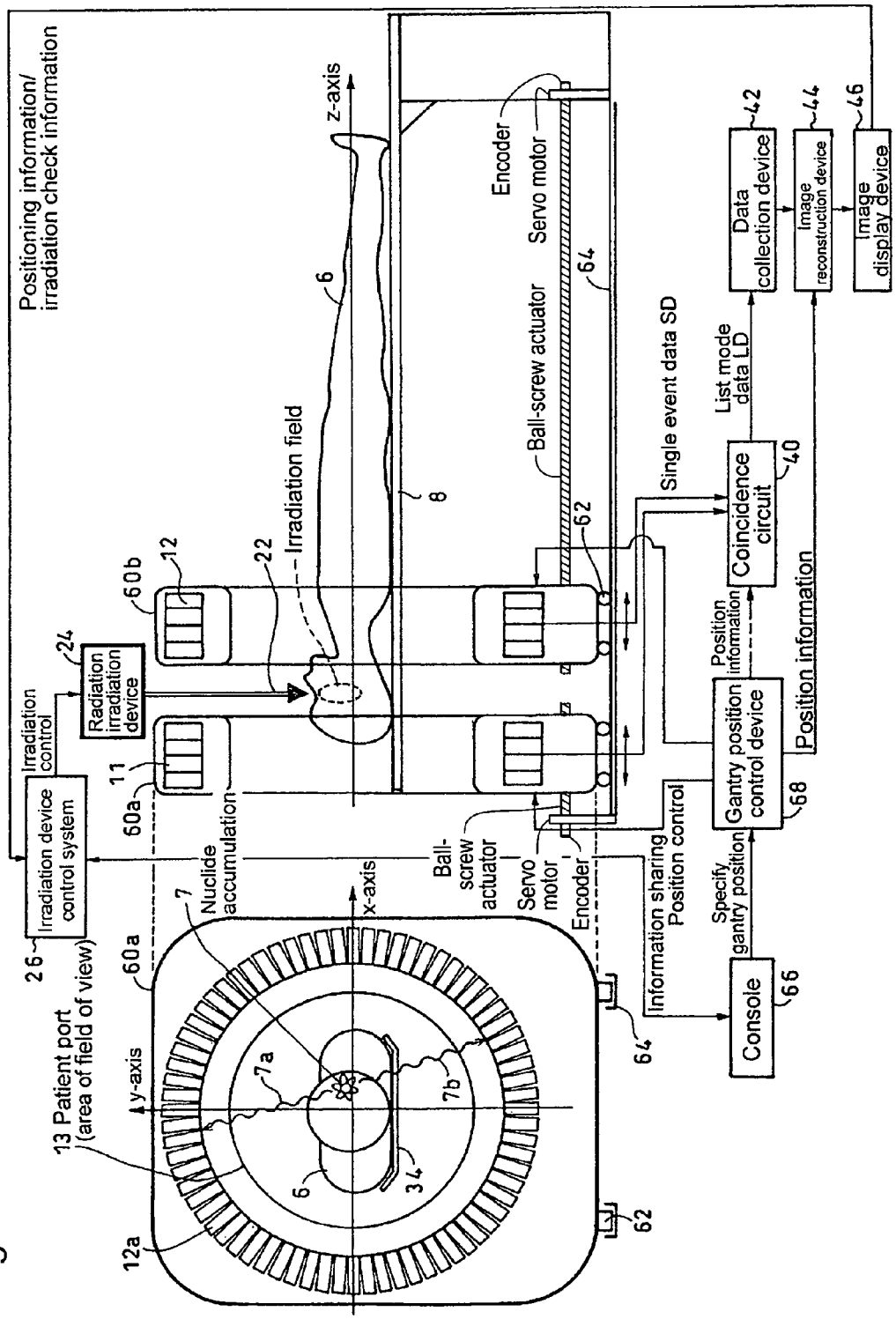
FIG. 14 is a diagram showing a first embodiment of the present invention.

Next, a description will be given of an embodiment of the present invention where the open PET device is applied to beam monitoring in radiation therapy. FIG. 14 shows the configuration of a first embodiment. Two identical ring-shaped detector rings (space-forming detector rings) 11 and 12 are arranged in parallel as independent gantries (60*a*, 60*b*), and a radiation irradiation device 24 is inserted into the space between the detector rings 11 and 12, whereby treatment monitoring of observing one and the same treated area immediately after treatment by PET is implemented.

Specifically, the embodiment includes the detector rings 11 and 12, gantry covers 60*a* and 60*b* which cover the respective detector rings, and a bed 8 on which a patient 6 lies. The gantries are each equipped with wheels 62, and have the function of moving in the direction of the body axis on common or different rails 64.

A therapy beam 22 produced from the radiation irradiation device 24 passes through the spatial gap area between the detector rings 11 and 12, and irradiates the irradiation field of the patient 6 without interfering with the PET gantries (60*a*, 60*b*).

In FIG. 14, the radiation irradiation device 24 and the PET device are controlled by an irradiation device control system 26, into which an irradiation plan program is input, and a gantry position control device 68. The irradiation device control system 26 includes irradiation position setting means for setting the irradiation position of the radiation, and radiation irradiating means for irradiating the irradiation position of the radiation with an irradiation beam. The gantry position control device 68 includes position setting means for setting movable detector ring positions, and sets the positions of the movable detector rings in the position setting means based on irradiation timing information on the radiation irradiating means.

The movable detector rings have moving means which includes a servo motor, a ball screw actuator, an encoder, the wheels 62, and the rails 64. The moving means moves the movable detector rings to set positions that are set by the position setting means.

The irradiation position setting means which controls an electromagnet, a collimator, a scatterer, a ridge filter, a slit, and the like sets an irradiation position in the irradiation field. The radiation irradiating means which projects X-rays or gamma rays irradiates the set position with the beam of predetermined shape.

The PET device measures radiations produced by the irradiation in the vicinity of the affected area, and reconstructs PET images based on the collected data. The resulting PET images are fed back to the irradiation device control system 26 and used for positioning the irradiation field, checking the effect of the treatment, and modifying the treatment plan.

Next, the method of processing the measured data will be described. Nuclides 7 in the body of the patient 6 emit pairs of annihilation radiations 7a and 7b which travel at angles of approximately 180° from each other in all directions. Single event data SD, which is the measured data on either one of a pair of annihilation radiations 7a and 7b, is transmitted from the detector rings 11 and 12 to a common coincidence circuit 40. The single event data SD is converted into list mode data LD which is the information on the coincidence pair between the detector rings 11 and 12.

The list mode data LD is stored by a data collection device 42 into a recording medium before transmitted to an image reconstruction device 44 for image reconstruction operation. The reconstructed image is then displayed by an image display device 46.

The movement of the detector rings 11 and 12 is controlled by the gantry position control device 68 based on gantry position information which is specified from a console device 66. The gantry position information is either included into the list mode data LD through the coincidence circuit 40 or directly transmitted to the image reconstruction device 44 so that the calculation for image reconstruction operation can be performed based on the actual position information on the detectors.

The detector rings measure the beam irradiation all the time. It is known that the beam irradiation can produce a large amount of prompt gamma rays which serve as noise components to the PET measurement. The data measured under the beam irradiation is not suitable for imaging. To prevent load on the data collection system, it is therefore desirable that the data collection step be provided after a data select step of selecting only data for image reconstruction. If the data collection system can bear more loads, the data select step may be provided after the data collection step.

Next, a description will be given of an embodiment of the present invention where a detector shift (approach shift) is applied. In some cases, only a single administration of beam irradiation may be sufficient. A plurality of administrations may sometimes be needed. Assume here that two-minute irradiations are performed at an interval of eight minutes. As mentioned previously, when the PET device detects annihilation radiations produced by the beam irradiation, consideration must be given to the following two points:

(1) The beam irradiation can cause damage to the detectors, such as a circuit breakdown.

(2) The nuclides produced by the beam irradiation have an extremely short half-life of several tens of seconds to 20 minutes.

Figure 15:
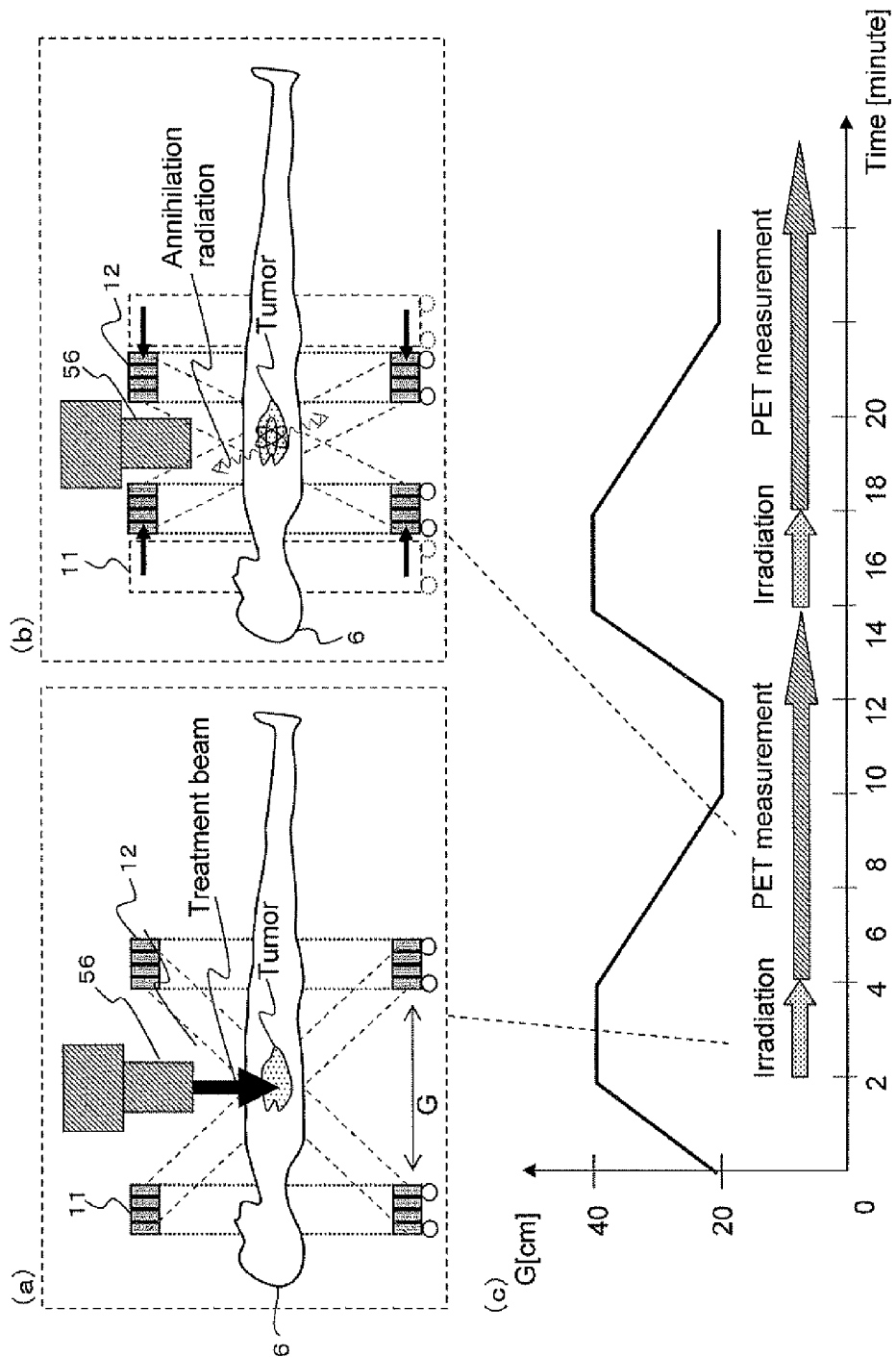
FIG. 15 is a diagram showing the operation of the first embodiment.

Then, as shown in FIG. 15, (a) the detector rings 11 and 12 are located away from the irradiation field while the beam irradiation is performed through an irradiation port 56. When the irradiation ends, (b) PET measurement is conducted while the detector rings 11 and 12 are moving closer with each other. Start moving immediately after the end of the irradiation, the detector rings 11 and 12 can quickly approach the irradiation field to measure all the radiations occurring from the short-lived nuclides. FIG. 15(c) shows an example of time variations of the open area width G, where (a) during irradiation, the detector rings 11 and 12 are located 40 cm apart, and (b) after irradiation, the detector rings 11 and 12 are moved to approach up to 20 cm. The foregoing movement may be applied not only to bolus irradiation but to spot scanning irradiation as well.

Figure 16:
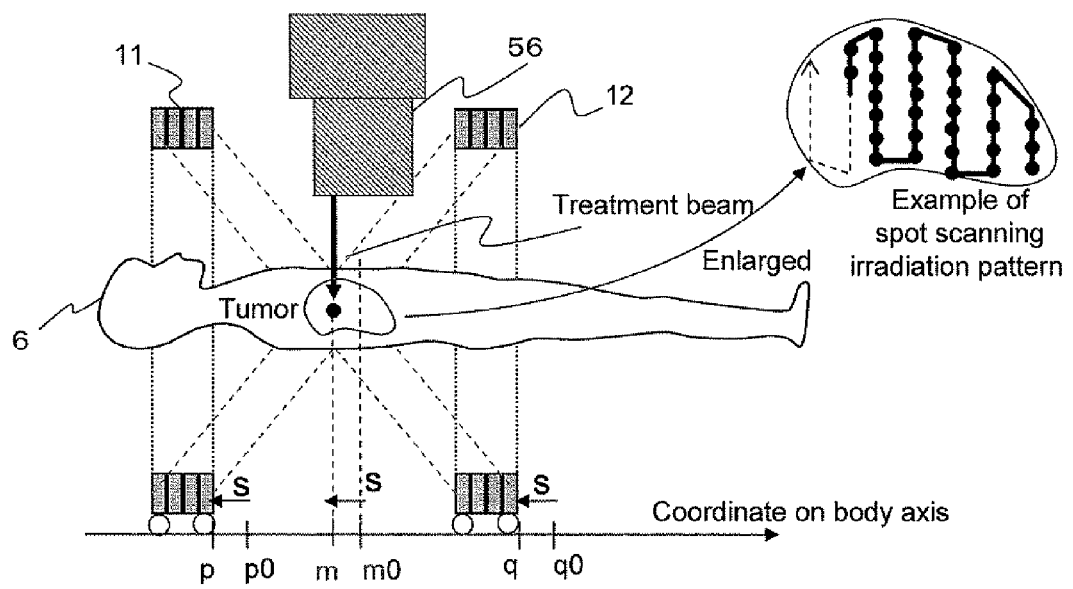
FIG. 16 is a diagram showing a second embodiment of the present invention.

Next, a second embodiment of the present invention where a detector shift (parallel shift) is applied to spot scanning irradiation will be shown in FIG. 16. The diagram shows the spot scanning irradiation in which the irradiation field is further divided into a plurality of layers of zones parallel to the detector rings. The layers are each scanned and irradiated with the beam spot, moving from one layer to another in succession. With the center of a tumor or other reference position as m0, the reference positions of the left and right detector rings when the center of the open area falls on m0 will be referred to as p0 and q0, respectively. In the spot scanning irradiation, the tumor is scanned with pencil beam irradiation in a short time so that the entire tumor is covered with spot-like irradiation fields. After the irradiation, the detector rings are parallel shifted in the direction of the body axis so as to follow the layer movement of the spot scanning irradiation, whereby the distribution of short-lived nuclides can be effectively detected to create precise images of the tumor and its periphery. Specifically, assuming that the current position of the irradiation field of the pencil beam is m (m=m0+s), the left and right detector rings are shifted by s so that their current positions come to p=p0+s and q=q0+s, respectively.

Figure 17:
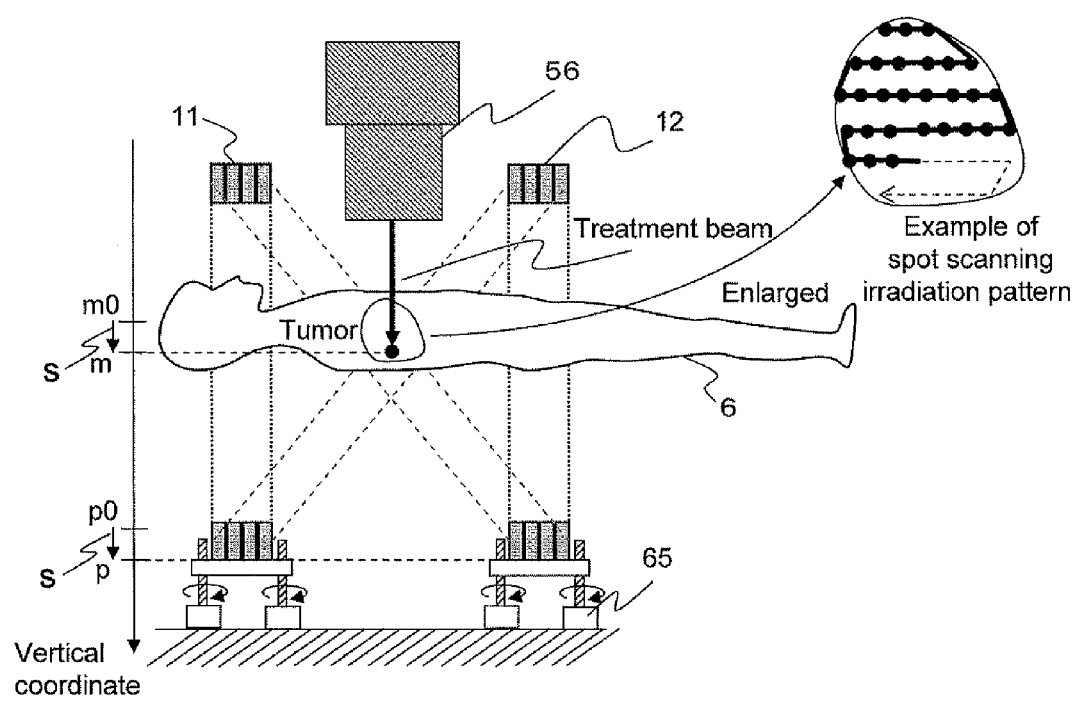
FIG. 17 is a diagram showing a third embodiment of the present invention.

FIG. 17 shows a spot scanning method in which the entire irradiation field is divided into a plurality of layers of zones perpendicular to the irradiation axis, and the layers are each scanned and irradiated with the beam spot, moving from one layer to another in succession. This provides a third embodiment where the detector rings 11 and 12 are moved (parallel shifted) in the direction of the irradiation axis in line with the vertical movement of the irradiation field of the spot scanning irradiation. With the tumor center or other reference position as m0, the reference vertical position of the detector rings 11 and 12 when the center of the open area falls on m0 will be referred to as p0. After the irradiation, the detector rings 11 and 12 are moved up and down in the direction of the irradiation axis so as to follow the layer movement of the spot scanning irradiation, whereby the distribution of short-lived nuclides can be effectively detected to create precise images of the tumor and its periphery. Specifically, assuming that the current position of the irradiation field of the pencil beam in the vertical direction is m (m=m0+s), the detector rings 11 and 12 are shifted by servo motors 65 by s so that their current positions come to p=p0+s. Both in the second embodiment and the third embodiment, it is preferred that the detector rings are controlled to follow the layer movement with a constant time difference from the irradiation of each layer. The distribution of short-lived nuclides can be detected more efficiently if the radiation irradiation is once suspended for PET measurement when the irradiation moves to a new layer.

While the second and third embodiments have dealt with the cases of moving both the detector rings 11 and 12, either one of the detector rings may be moved alone.

Figure 18:
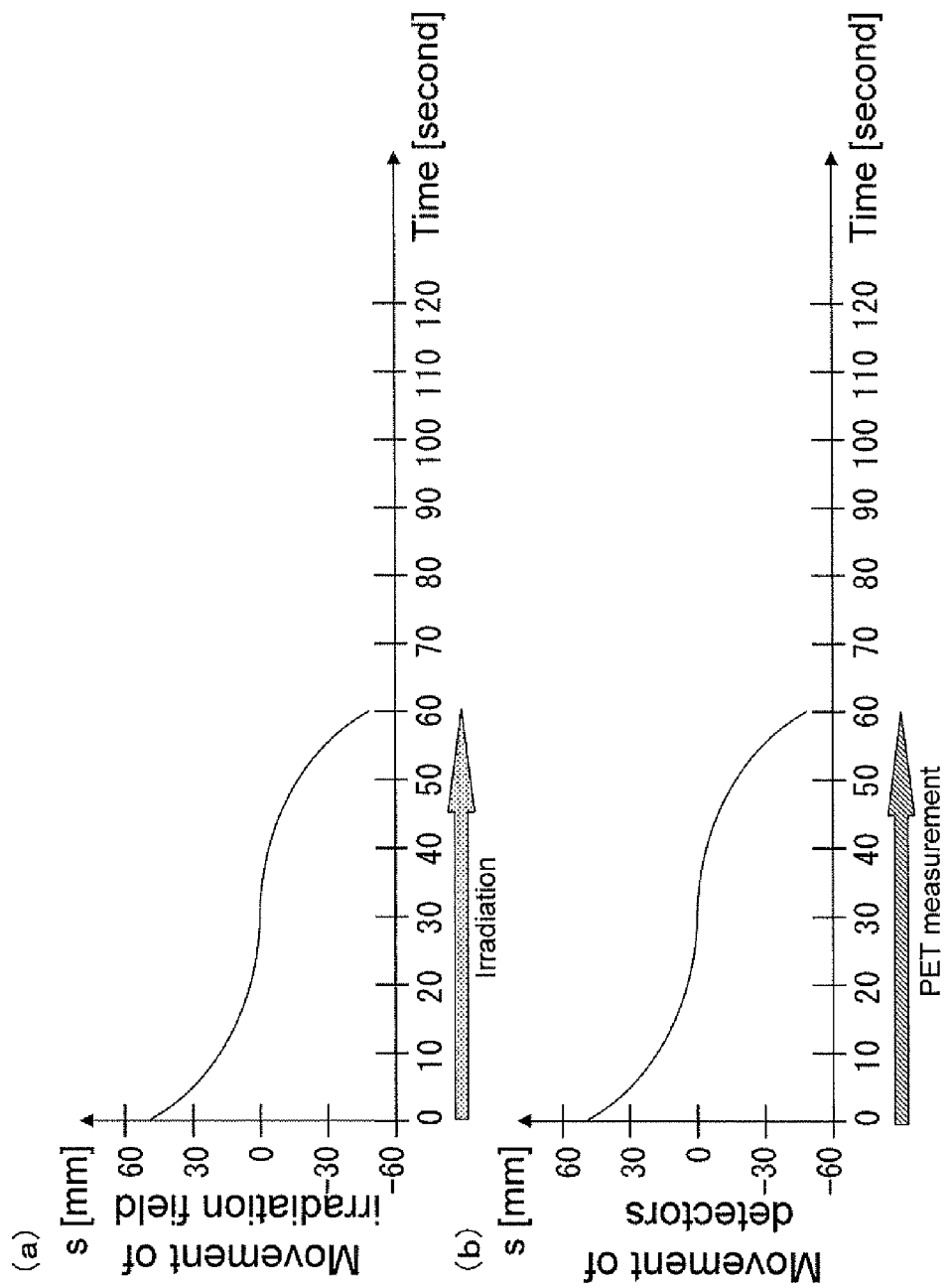
FIG. 18 is a diagram showing an example of the moving patterns of the irradiation field and the detectors according to the second and third embodiments.

FIG. 18 shows an example of the moving patterns of the irradiation field and the detectors according to the embodiments shown in FIGS. 16 and 17. FIG. 18(*a*) shows an example where the irradiation field is moved to cover an affected area having a width of approximately 100 mm in 60 seconds. FIG. 18(*b*) shows the pattern of movement of the detectors. The detectors (rings) are moved to follow the movement of the irradiation field, and measurement is performed simultaneously with the irradiation. Since the irradiation produces a large amount of prompt gamma rays which serve as noise components to the PET measurement, PET images are in fact created only from data that is measured in short intervals between irradiations which occur periodically or non-periodically during the irradiation.

Figure 19:
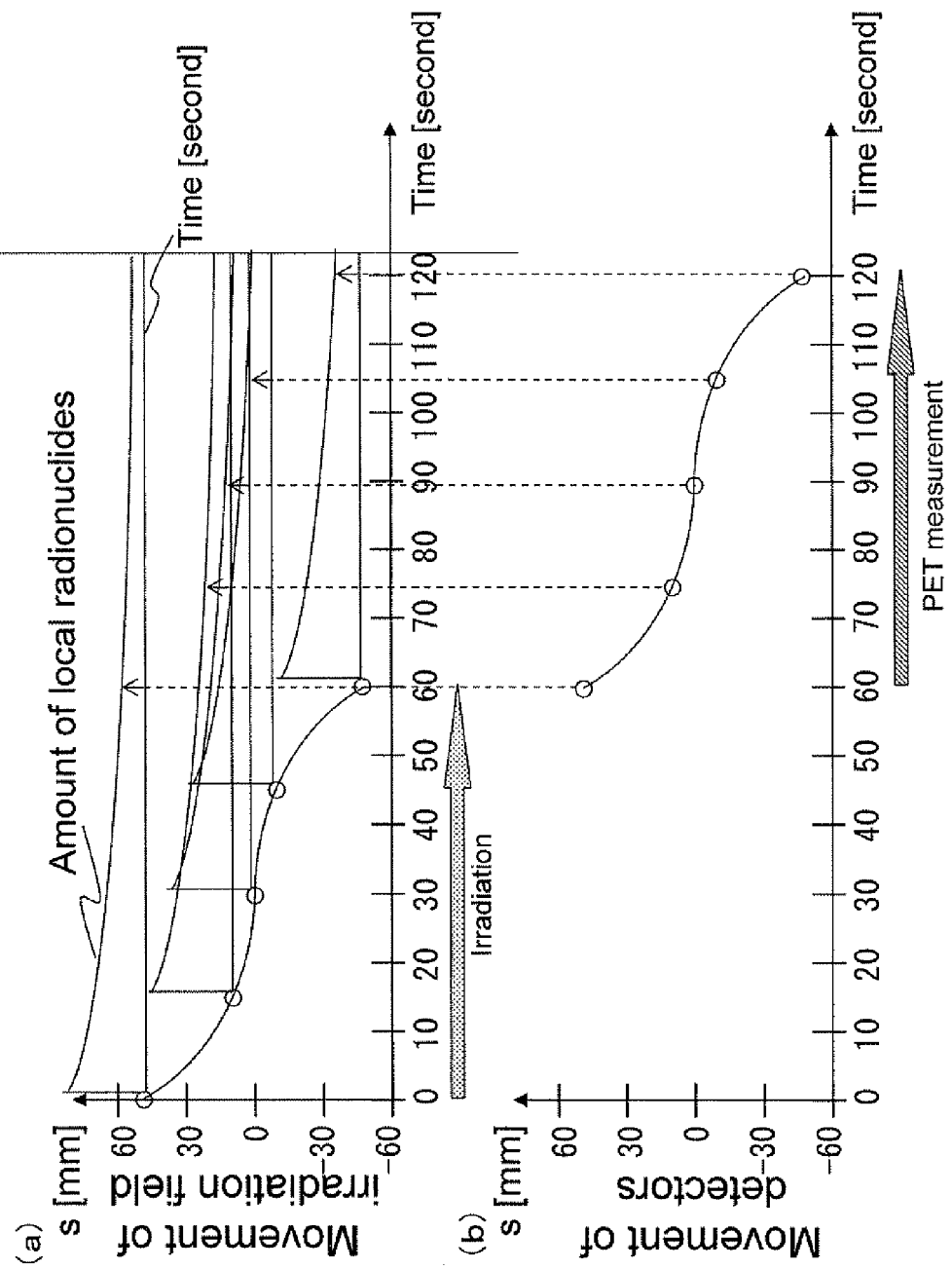
FIG. 19 is a diagram showing another example of the moving patterns of the irradiation field and the detectors according to the second and third embodiments.

FIG. 19 shows an example of the patterns where the detectors are moved to follow the movement of the irradiation field after the end of a series of irradiations. Since the PET measurement is performed after the end of the irradiations, only the data that is unaffected by prompt gamma rays is collected. The nuclides produced by the irradiation have a half-life of several tens of seconds to several minutes or so. If the local irradiations are performed with time shifts, there are nuclides with various degrees of attenuation at a point in time after the end of the irradiations. Then, the detectors are moved to follow the irradiation positions after a certain time difference corresponding to the duration of the series of irradiations (in the example of FIG. 19, 60 seconds) so as to suppress variations in attenuation depending on the irradiation positions.

For chest treatment and the like, respiratory and other movements of the affected area need to be taken into account. Specifically, the treatment plan is created so as to administer irradiations in a relatively stable phase of breathing such as the expiratory state in the respiratory cycle. In treatment, respiration monitoring is performed to detect the motion of a marker or the like attached to the chest or the proximity of the irradiation area, and irradiation is administered only when the respiratory phase coincides with that on the treatment plan.

Figure 20:
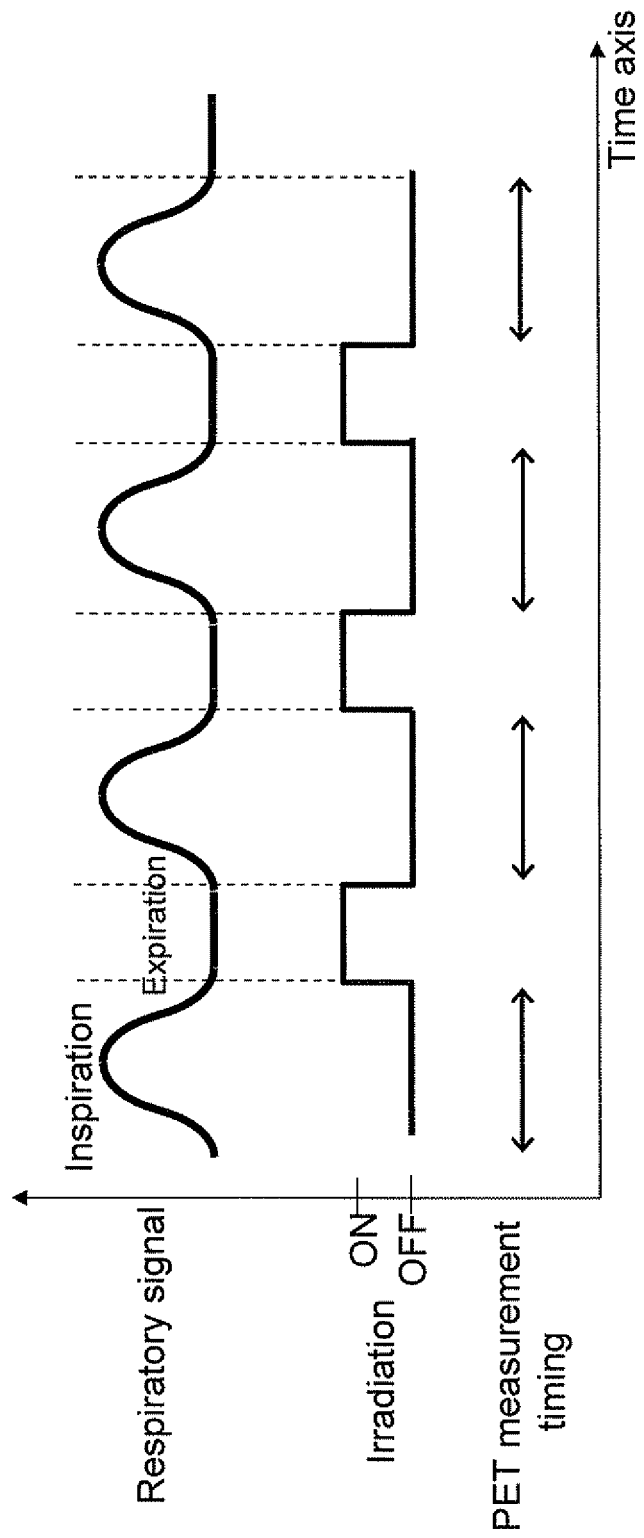
FIG. 20 is a time chart showing an example of respiratory-gated control.

FIG. 20 shows the control of turning ON the irradiation depending on the expiration phase of the respiratory signal. Here, PET measurement can be performed at the timing when the irradiation is OFF (inspiration phase). This allows efficient PET measurement in the middle of a series of irradiations.

Figure 21:
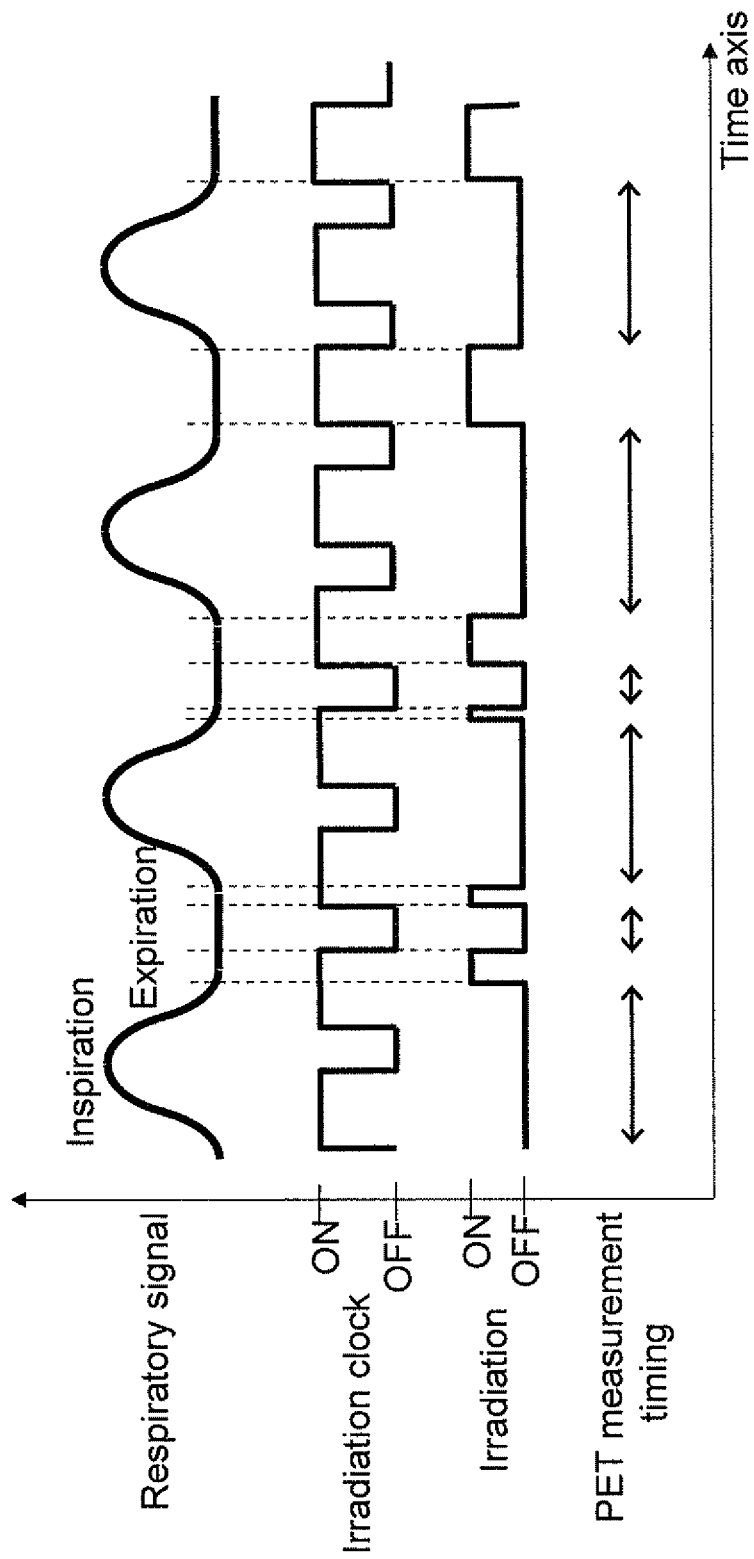
FIG. 21 is a time chart showing another example of the respiratory-gated control.

FIG. 20 is predicated on the case that the irradiation beam can be continuously produced from the accelerator. However, the irradiation beam may be produced intermittently in a periodical manner. FIG. 21 shows the latter case where respiratory-gated irradiation is performed. The irradiation can be performed only when the expiration phase coincides with the irradiation clock. This consequently limits the timing available for irradiation as compared to the case of FIG. 20, whereas the timing available for PET measurement increases and it is possible to collect more PET measurement data. It should be appreciated that the body motions to be taken into account for treatment are not limited to respirations but include heartbeats and other motions.

Figure 22:
FIG. 22 is a time chart showing the operation of the respiratory-gated control.

According to a flowchart shown in FIG. 22(A), the detectors initially detect radiations (S11). A coincidence determination is made by known techniques (S12). At the same time, respiration monitoring data which is obtained by detecting and analyzing the motion of the marker arranged in the vicinity of the radiation irradiation area is consulted (S13). A phase other than expiration phases is selected (S14), and data that is determined to be coincident is collected (S15). When the irradiation is ended (S16), image reconstruction is performed based on the collected data (S17) and the image is output (S18).

There has so far been no case where the PET-based measurement is applied to respiratory-gated irradiation. FIG. 22(B) shows the flowchart of a conventional method of PET-based measurement with ordinary, non-respiratory-gated irradiation. With the conventional technique, accelerator information has been consulted at step S23 instead of the respiration monitoring data. According to the present invention, the direct consultation of the respiration monitoring data makes it possible to collect more information with high precision and acquire synchronous data for PET measurement easily without interfering with the irradiation system. PET image reconstruction can be performed in each respiratory phase to suppress respiration-based fluctuations of the PET images.

Now, a description will be given of a fourth embodiment which is another mode of operation of the basic two detector rings and radiation irradiation device shown in FIGS. 4 and 5(B).

Figure 23:
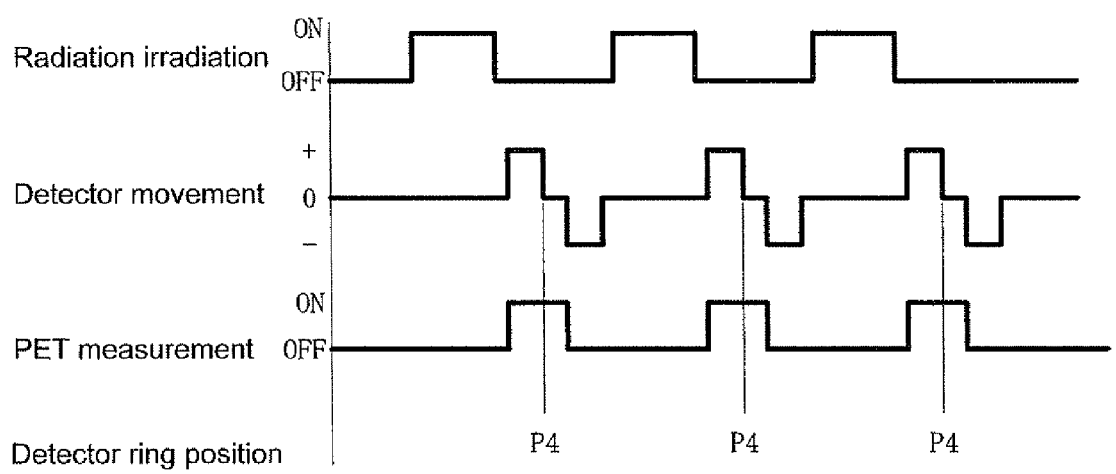
FIG. 23 is a time chart showing the operation of a fourth embodiment of the present invention.

On the time chart shown in FIG. 5(B), the detector rings move on the approach to reach the predetermined position (P4) closest to the irradiation field and then immediately move on the return. FIG. 23 shows a time chart where the detector rings reaching the position make a stop until the end of the PET measurement, and then move on the return to their retracted position.

Next, a fifth embodiment shown in FIG. 24, which allows a quicker approach to the irradiation field after irradiation, will be described.

Figure 25:
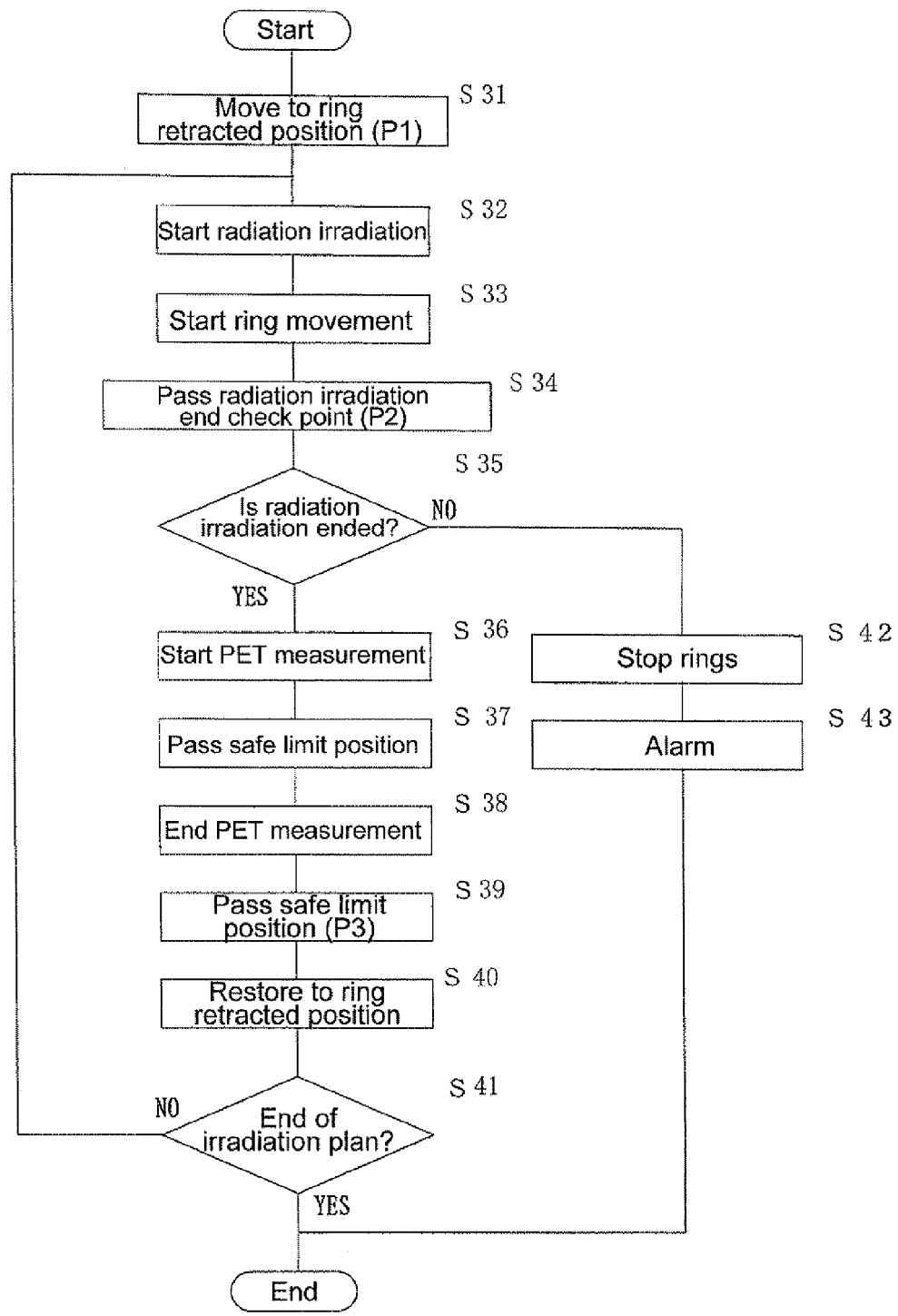
FIG. 25 is a flowchart showing the operation of the fifth embodiment.

FIG. 25 shows the flowchart of a program which: moves the detector rings to the retracted position in advance (S31); starts moving the detector rings on the approach from the retracted position toward the irradiation field before the radiation irradiation (S32) ends, based on a back calculation from the radiation stop time (S33); makes the detector rings pass a safe limit position (a farthest position from the irradiation field where damage can result if during the radiation irradiation) after the end of the irradiation (S37); and makes the detector rings approach closest to the irradiation field, move on the return, pass the safe limit position again, and return to the retracted positions (S40).

Figure 24:
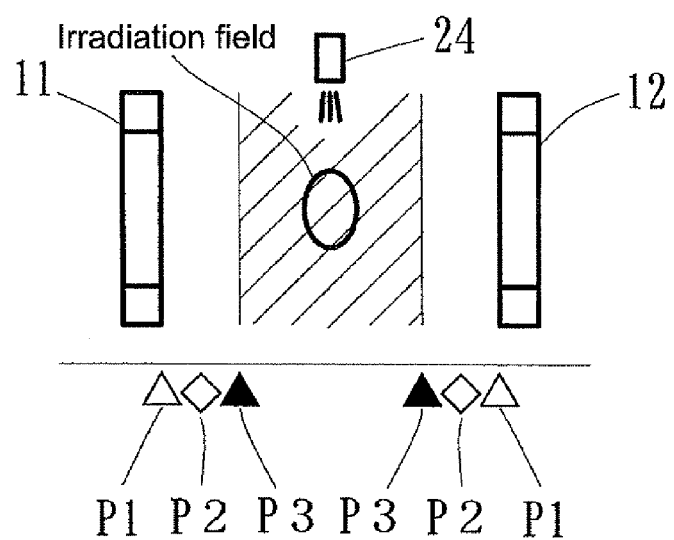
FIG. 24 is a diagram showing a fifth embodiment of the present invention.

For safety's sake, a radiation irradiation end check position (P2) is established roughly in the middle between the retracted position (P1) and the safe limit position (P3) shown in FIG. 24. The program is written so that the radiation irradiation is ended by the time when the detector rings pass the radiation irradiation end check position on the approach. As soon as the detector rings pass the irradiation end check position (S34), it is checked whether the radiation irradiation is ended. If ended (S35/YES), the detector rings are simply let to pass. If not ended yet (S35/NO), which suggests an abnormal condition, the detector rings are stopped before going over the safe limit position (S42). An alarm is issued as well (S43). Since the detector rings start being moved on the approach from the retracted position toward the irradiation field (S33) before the end of the radiation irradiation (S32), the detector rings can pass the safe limit position at higher speed than with the programs of the time charts shown in FIG. 5(B) and FIG. 23. This makes it possible to approach the irradiation field in a shorter time.

The next radiation irradiation, if any, is started after the detector rings pass the safe limit position on the return. The PET measurement is effective (S38) from when the radiation irradiation check position is passed on the approach (S36) until before the safe limit position is passed on the return (S39). The routine of steps S32 to S40 is repeated (S41) until the end of the irradiation plan.

The safe limit position varies depending on such factors as the setting condition of the radiation irradiation, and is primarily determined by experience or experiment. For example, such a position can be determined in a radiation irradiation test by placing the detector rings at a sufficient distance from the irradiation field and gradually moving the detector rings toward the irradiation field for measurement.

In order to deal with the abnormal condition of step 35/NO, the detector rings may be stopped (S42) before going over the safe limit position. After a predetermined time (e.g., after one second), whether the radiation irradiation is ended may be checked again (S35). An alarm may be issued (S43) if the radiation irradiation is not ended within a predetermined number of times of checking.

The PET measurement may be continued until immediately before the start of the next irradiation (S32), instead of being ended (S38) before the safe limit position is passed (S39).

Figure 26:
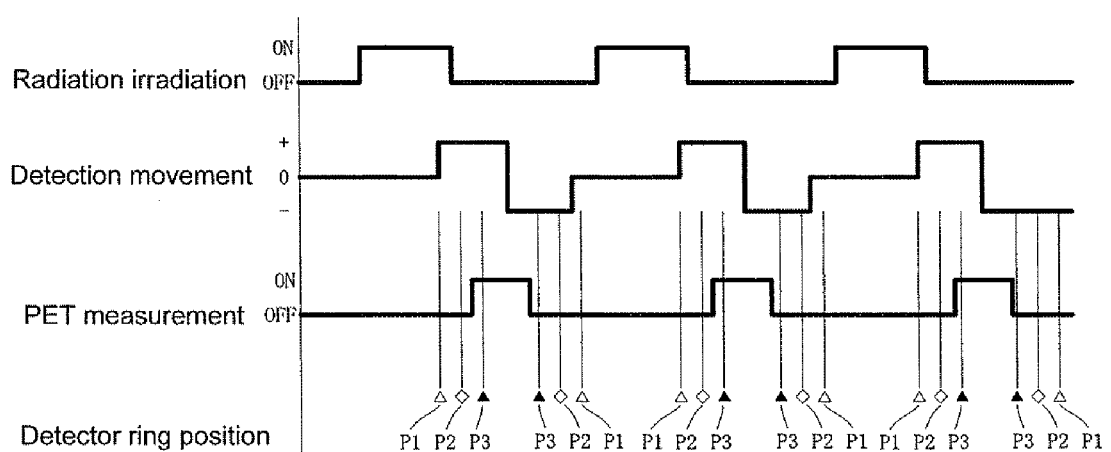
FIG. 26 is a time chart showing the operation of the fifth embodiment.

FIG. 26 is a time chart showing the operation timing of each component in the flowchart of FIG. 25.

INDUSTRIAL APPLICABILITY

In the radiation therapy beam monitoring device for detecting annihilation radiations produced by beam irradiation, radiation measurement can be performed by quickly moving or while moving the detectors, which are located away from the irradiation field during the beam irradiation, toward the irradiation field after the end of the beam irradiation. This makes it possible to prevent a performance degradation or a failure of the detectors due to the beam irradiation, and create a precise image of the distribution of short-lived nuclides in the vicinity of the irradiation field.

The invention claimed is:

1. A detector-shift type combined radiation therapy/PET apparatus for applying radiation to a body, the apparatus comprising:
   an open PET device including a plurality of detector rings that are arranged to be opposed to each other in a direction of an axis of the body, the open PET device being structured to perform radiation measurement inside bores of the rings;
   a radiation irradiation device that is capable of irradiation with radiation through a space defined by two mutually-adjoining detector rings, thereby forming an irradiation field in the space;
   rails, wherein at least either one of the two mutually-adjoining detector rings is a movable detector ring disposed on the rails, and the movable detector ring is located in a retracted position on the rails away from the irradiation field so as to avoid damage from irradiation during the radiation irradiation; and
   a gantry position control device controlling movement of the moveable detector ring such that the movable detector ring performs radiation measurement while moving on the rails on an irradiation-field side of the retracted position after the irradiation.

2. The detector-shift type combined radiation therapy/PET apparatus according to claim 1, wherein
   the retracted position of the movable detector ring is at a predetermined distance on a safe side of a safe limit position, the safe limit position being a limit position closer to the irradiation field where irradiation-based damage to the moveable detector ring is prevented during the radiation irradiation, and
   the movable detector ring starts moving from the retracted position toward the irradiation field during irradiation based on a back calculation from a radiation irradiation stop time and passes the safe limit position after an end of the irradiation.

3. The detector-shift type combined radiation therapy/PET apparatus according to claim 1, wherein
   the radiation irradiation device generates a spot beam that divides the irradiation field into a plurality of layers of zones and scans and irradiates each layer; and
   the moveable detector ring moves from one layer to another in succession, and is structured to perform radiation measurement while moving so as to follow layer movement of the irradiation.

4. The detector-shift type combined radiation therapy/PET apparatus according to claim 3, wherein
   the moveable detector ring is structured to perform radiation measurement after an end of a series of irradiations while the detector ring is moved to follow the layer movement of the irradiation with a certain time difference from the irradiation.

5. The detector-shift type combined radiation therapy/PET apparatus according to claim 3, wherein
   the moveable detector ring performs the radiation measurement when the radiation irradiation moves to a new layer and the radiation irradiation is once suspended.

6. The detector-shift type combined radiation therapy/PET apparatus according to claim 1, wherein the movable detector ring moves in the direction of the axis of the body.

7. The detector-shift type combined radiation therapy/PET apparatus according to claim 1, wherein the movable detector ring moves in a direction along a plane perpendicular to the direction of the axis of the body.

8. The detector-shift type combined radiation therapy/PET apparatus according to claim 7, wherein the movable detector ring moves in a direction of an irradiation axis of the radiation.

9. The detector-shift type combined radiation therapy/PET apparatus according to claim 1, wherein in respiratory-gated irradiation of performing irradiation with the radiation in synchronization with respiratory cycles, the moveable detector ring performs radiation measurement over time intervals between radiation irradiations, the apparatus further comprises means for respiration monitoring for determining the interval for radiation irradiations.

10. The detector-shift type combined radiation therapy/PET apparatus according to claim 9, wherein the moveable detector ring performs radiation irradiation in a stable region of a respiratory cycle of the body, and performance radiation measurement in an unstable region of the respiratory cycle where the radiation irradiation is not practical.

* * * * *